US012723051B2

(12) United States Patent
Jung et al.

(10) Patent No.: US 12,723,051 B2

(45) **Date of Patent: *Sep. 1, 2026**

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boon Jae Jang, Daejeon (KR); Sang Duk Suh, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 758 days.

This patent is subject to a terminal disclaimer.

(21) Appl. No.: 17/286,423

(22) PCT Filed: Nov. 29, 2019

(86) PCT No.: PCT/KR2019/016776

§ 371 (c)(1),
(2) Date: Apr. 16, 2021

(87) PCT Pub. No.: WO2020/111886

PCT Pub. Date: Jun. 4, 2020

(65) Prior Publication Data

US 2021/0388001 A1 Dec. 16, 2021

(30) Foreign Application Priority Data

Nov. 30, 2018 (KR) ........................ 10-2018-0152914
Nov. 27, 2019 (KR) ........................ 10-2019-0154681

(51) Int. Cl.

| | |
|---|---|
| ***C07D 519/00*** | (2006.01) |
| ***C07D 405/14*** | (2006.01) |
| ***C07D 409/14*** | (2006.01) |
| ***H10K 50/11*** | (2023.01) |
| ***H10K 85/60*** | (2023.01) |
| ***H10K 101/00*** | (2023.01) |
| ***H10K 101/10*** | (2023.01) |

(52) U.S. Cl.

CPC ......... *C07D 519/00* (2013.01); *C07D 405/14* (2013.01); *C07D 409/14* (2013.01); *H10K 85/654* (2023.02); *H10K 85/6572* (2023.02); *H10K 85/6574* (2023.02); *H10K 85/6576* (2023.02); *H10K 50/11* (2023.02); *H10K 2101/10* (2023.02); *H10K 2101/90* (2023.02)

(58) Field of Classification Search

CPC .. C07D 519/00; C07D 405/14; C07D 409/14; H10K 85/654; H10K 85/6572; H10K 85/6574; H10K 85/6576; H10K 50/11; H10K 2101/10; H10K 2101/90

See application file for complete search history.

(56) References Cited

U.S. PATENT DOCUMENTS

| | | | | |
|---|---|---|---|---|
| 11,807,632 | B2 * | 11/2023 | Jung | C07D 409/14 |
| 2004/0251816 | A1 | 12/2004 | Leo et al. | |
| 2011/0309343 | A1 | 12/2011 | Langer et al. | |
| 2012/0223276 | A1 | 9/2012 | Parham et al. | |
| 2015/0073147 | A1 * | 3/2015 | Inoue | H10K 85/6572 549/43 |
| 2015/0171340 | A1 * | 6/2015 | Lee | H10K 85/6574 544/333 |
| 2016/0226001 | A1 | 8/2016 | Parham et al. | |
| 2016/0329506 | A1 | 11/2016 | Lee et al. | |
| 2017/0186965 | A1 * | 6/2017 | Parham | C07D 405/10 |
| 2020/0377489 | A1 * | 12/2020 | Lee | C07D 407/14 |
| 2021/0139469 | A1 | 5/2021 | Jung et al. | |
| 2023/0157151 | A1 * | 5/2023 | Parham | H10K 50/82 252/301.16 |

(Continued)

FOREIGN PATENT DOCUMENTS

| | | |
|---|---|---|
| CN | 102850334 A | 1/2013 |
| CN | 103232843 A | 8/2013 |

(Continued)

OTHER PUBLICATIONS

Tao, Wen-Wen, et al. "Dibenzofuran/dibenzothiophene as the secondary electron-donors for highly efficient blue thermally activated delayed fluorescence emitters." Journal of Materials Chemistry C 7.15 (2019): 4475-4483. (Year: 2019).*

(Continued)

*Primary Examiner* — Dawn L Garrett

(74) *Attorney, Agent, or Firm* — Bryan Cave Leighton Paisner LLP

(57) ABSTRACT

A heterocyclic compound represented by Chemical Formula 1, and an organic light emitting device including the same, and the heterocyclic compound providing improved efficiency, low driving voltage, and improved lifetime characteristics of the organic light emitting device.

[Chemical Formula 1]

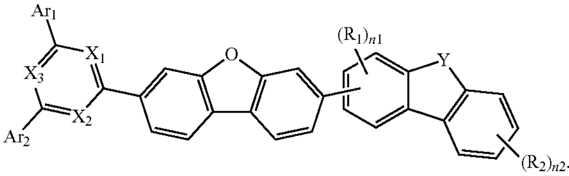

9 Claims, 1 Drawing Sheet

(56) References Cited

U.S. PATENT DOCUMENTS

| | | | | |
|---|---|---|---|---|
| 2023/0172064 A1* | 6/2023 | Ahn | H10K 85/40 257/40 |
| 2023/0263054 A1* | 8/2023 | Hwang | H10K 85/633 257/40 |
| 2023/0301183 A1* | 9/2023 | Lee | H10K 85/6574 257/40 |
| 2023/0371371 A1* | 11/2023 | Lee | C09K 11/025 |

FOREIGN PATENT DOCUMENTS

| | | | | | |
|---|---|---|---|---|---|
| CN | 108191842 | A | * | 6/2018 | C07D 409/14 |
| JP | 2017-107992 | A | | 6/2017 | |
| KR | 10-2000-0051826 | A | | 8/2000 | |
| KR | 10-2012-0104246 | A | | 9/2012 | |
| KR | 10-2015-0083385 | A | | 7/2015 | |
| KR | 20180061076 | A | * | 6/2018 | |
| KR | 10-2018-0124735 | A | | 11/2018 | |
| KR | 10-2019-0079340 | A | | 7/2019 | |
| KR | 10-2235480 | B1 | | 4/2021 | |
| WO | 03012890 | A2 | | 2/2003 | |
| WO | 2015036080 | A1 | | 3/2015 | |
| WO | 2015105251 | A1 | | 7/2015 | |
| WO | WO-2019132374 | A1 | * | 7/2019 | |

OTHER PUBLICATIONS

Kang, Yu Jin, Si Hyun Han, and Jun Yeob Lee. "Lifetime enhancement of blue thermally activated delayed fluorescent devices by separated carrier channels using dibenzofuran-triazine type hosts." Journal of industrial and engineering chemistry 62 (2018): 258-264. (Year: 2018).*

Machine translation of CN 108191842 (publication date: Jun. 2018) (Year: 2018).*

* cited by examiner

【FIG. 1】
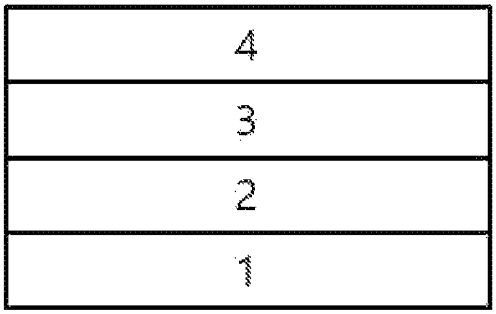
【FIG. 2】
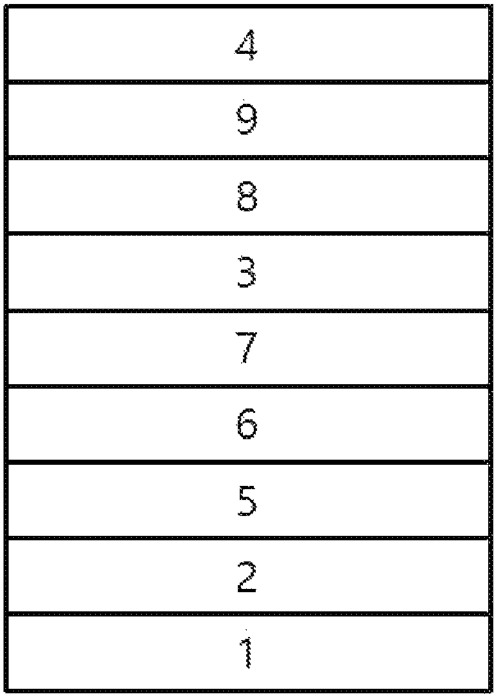

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/016776 filed on Nov. 29, 2019, which claims priority to Korean Patent Application No. 10-2018-0152914 filed on Nov. 30, 2018, and Korean Patent Application No. 10-2019-0154681 filed on Nov. 27, 2019, the disclosures of which are incorporated herein by reference in their entireties.

TECHNICAL FIELD

The present disclosure relates to novel compounds and organic light emitting devices including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, holes are injected from an anode into the organic material layer and electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

RELATED ARTS (Patent Literature 0001) Korean Patent Laid-open Publication No. 10-2000-0051826

DETAILED DESCRIPTION

Technical Problem

It is an object of the present disclosure to provide a novel compound and an organic light emitting device including the same.

Technical Solution in one aspect of the invention, the present disclosure provides a compound represented by the following Chemical Formula 1.

[Chemical Formula 1]

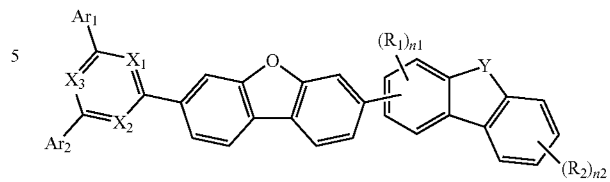

In Chemical Formula 1, $X_1$ to $X_3$ are each independently N or CH, and at least two of $X_1$ to $X_3$ are N, Y is P or S, and $Ar_1$ and $Ar_2$ are each independently phenyl, biphenylyl, naphthyl, phenanthrenyl, dimethylfluorenyl, carbazolyl, carbazolylphenyl, dibenzofuranyl, or dibenzothiophenyl, wherein, $Ar_1$ and $Ar_2$ are each independently unsubstituted or substituted with one or more substituents each independently selected from the group consisting of a $C_{1-20}$ alkyl, a $C_{6-20}$ aryl, and a $C_{2-20}$ heteroaryl containing one or more heteroatoms selected from the group consisting of N, O, and S, wherein $Ar_1$ and $Ar_2$ are not phenyl simultaneously, $R_1$ and $R_2$ are each independently a substituted or unsubstituted $C_{6-60}$ aryl; or a substituted or unsubstituted $C_{2-60}$ heteroaryl containing one or more heteroatoms selected from the group consisting of N, O, and S, n1 is an integer of 0 to 3, n2 is an integer of 0 to 4, and when n1 and n2 are two or more, the structures in parentheses are the same as or different from each other.

In another aspect of the invention, the present disclosure provides an organic light emitting device including: a first electrode; a second electrode provided to face the first electrode; and one or more organic material layers provided between the first electrode and the second electrode, wherein one or more layers of the organic material layers includes the compound represented by Chemical Formula 1.

Advantageous Effects

The compound represented by Chemical Formula 1 described above can be used as a material of an organic material layer of an organic light emitting device, and may improve efficiency, achieve a low driving voltage, and/or improve lifetime characteristics in the organic light emitting device.

DESCRIPTION OF DRAWINGS

FIG. 1 depicts an example of an organic light emitting device including a substrate 1, an anode 2, a light emitting layer 3, and a cathode 4.

FIG. 2 depicts an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4.

DETAILED DESCRIPTION

Hereinafter, the present disclosure will be described in more detail to help understanding of the present disclosure.

Definition of Terms

As used herein,

means a bond connected to another substituent group.

As used herein, the term "substituted or unsubstituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group containing at least one of N, O, and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group, and may be interpreted as a substituent to which two phenyl groups are linked.

As used herein, the number of carbon atoms of a carbonyl group is not particularly limited, but is preferably 1 to 40. Specifically, the carbonyl group may be a compound having the following structural formulae, but is not limited thereto.

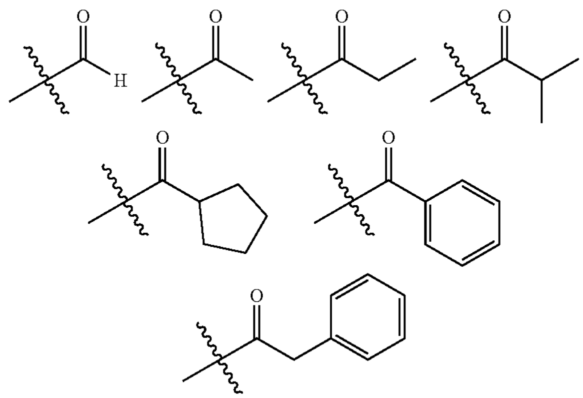

As used herein, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulae, but is not limited thereto.

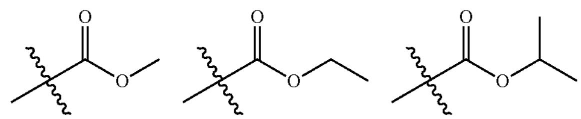

-continued

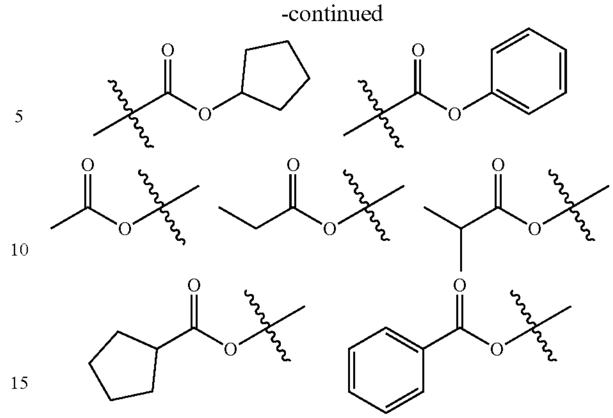

As used herein, the number of carbon atoms of an imide group is not particularly limited, but is preferably 1 to 25. Specifically, the imide group may be a compound having the following structural formulae, but is not limited thereto.

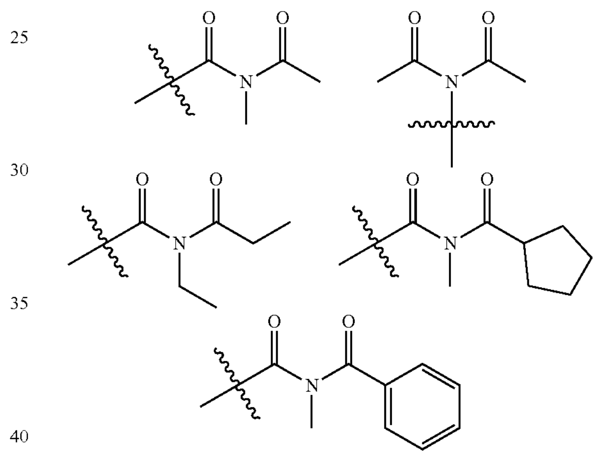

As used herein, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

As used herein, a boron group specifically includes a trimethylboron group, a triethylboron group, a t-butyldimethylboron group, a triphenylboron group, and a phenylboron group, but is not limited thereto.

As used herein, examples of a halogen group include fluorine, chlorine, bromine, and iodine.

As used herein, the alkyl group may be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to a further embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

As used herein, the alkenyl group may be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

As used herein, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

As used herein, an aryl group is not particularly limited, but preferably has 6 to 60 carbon atoms, and may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group, or the like, but are not limited thereto.

As used herein, a fluorenyl group may be substituted, and two substituent groups may be bonded to each other to form a spiro structure. In the case where the fluorenyl group is substituted,

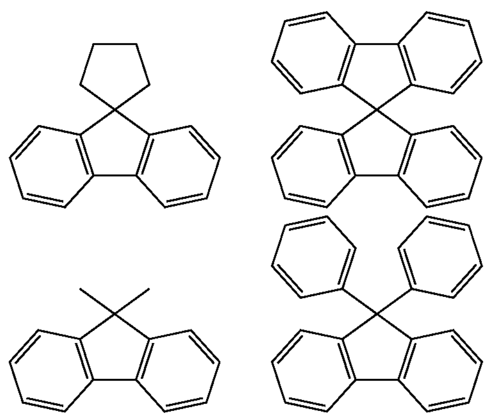

-continued

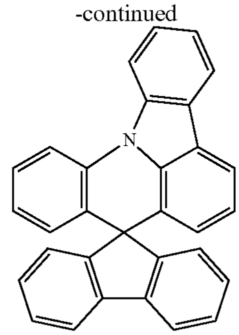

and the like can be formed. However, the structure is not limited thereto.

As used herein, a heteroaryl is a heteroaryl including one or more of O, N, Si, and S as a heteroatom, and the number of carbon atoms thereof is not particularly limited, but is preferably 2 to 60. Examples of the heteroaryl include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

As used herein, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

Compound

Meanwhile, the present disclosure provides a compound represented by Chemical Formula 1 described above.

The compound represented by Chemical Formula 1 has a structure in which the N-containing 6-membered heterocyclic group is substituted at position 3 of the dibenzofuran core, and the dibenzofuranyl group or dibenzothiophenyl group is substituted at position 7. Unlike compounds with the substituents at positions 2 and 7 and positions 4 and 7 of the dibenzofuran core, with the compounds with the substituents at positions 3 and 7 of the dibenzofuran core as above, there is an advantage that the compound has excellent electrochemical stability when a voltage is applied. Thus, driving voltage, efficiency, and lifetime characteristics of the organic light emitting device employing the compound represented by Chemical Formula 1 can be improved.

At this time, in Chemical Formula 1, $Ar_1$ and $Ar_2$ cannot simultaneously be phenyl. Herein, the meaning of "$Ar_1$ and $Ar_2$ cannot simultaneously be phenyl" means that $Ar_1$ and $Ar_2$ are not unsubstituted phenyl groups at the same time. That is, in Chemical Formula 1, the N-containing 6-membered heterocyclic group that is substituted with diphenyl cannot be substituted at position 3 of the dibenzofuran core. Specifically, in the case of a compound in which $Ar_1$ and $Ar_2$ are both phenyl, there may be a problem in the electrochemical stability of the compound. Thus, when a voltage is applied to the organic light emitting device employing it, the device characteristics may be deteriorated.

The compound represented by Chemical Formula 1 can be represented as follows according to the bonding position of a substituent substituted at position 7 of the dibenzofuran:

[Chemical Formula 1A]

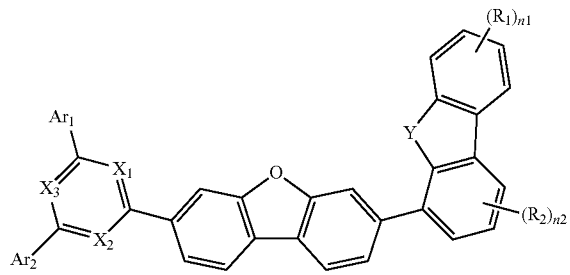

[Chemical Formula 1B]

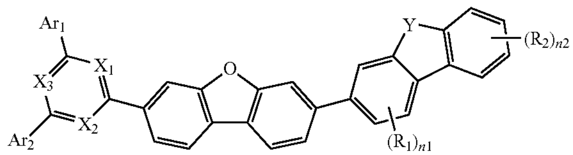

[Chemical Formula 1C]

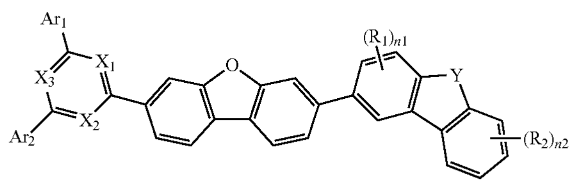

-continued

[Chemical Formula 1D]

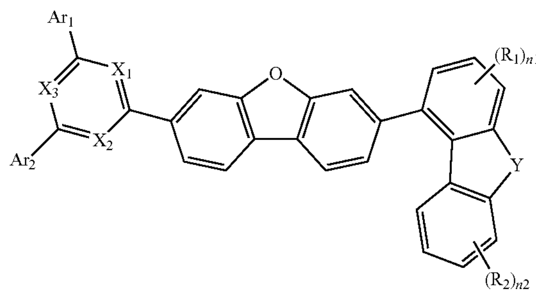

wherein, Chemical Formula 1A to 1D, the definition of each substituent is the same as those defined in Chemical Formula 1 above.

Preferably, $X_1$ to $X_3$ may be N.

Preferably, $Ar_1$ and $Ar_2$ may each independently be phenyl, biphenylyl, naphthyl, phenanthrenyl, dimethylfluorenyl, carbazolyl, carbazolylphenyl, dibenzofuranyl, or dibenzothiophenyl, wherein, $Ar_1$ and $Ar_2$ may each independently be unsubstituted or substituted with one or more substituents each independently selected from the group consisting of methyl, phenyl, carbazolyl, dibenzofuranyl, and dibenzothiophenyl.

Further preferably, $Ar_1$ and $Ar_2$ may each independently be any one selected from the group consisting of the following:

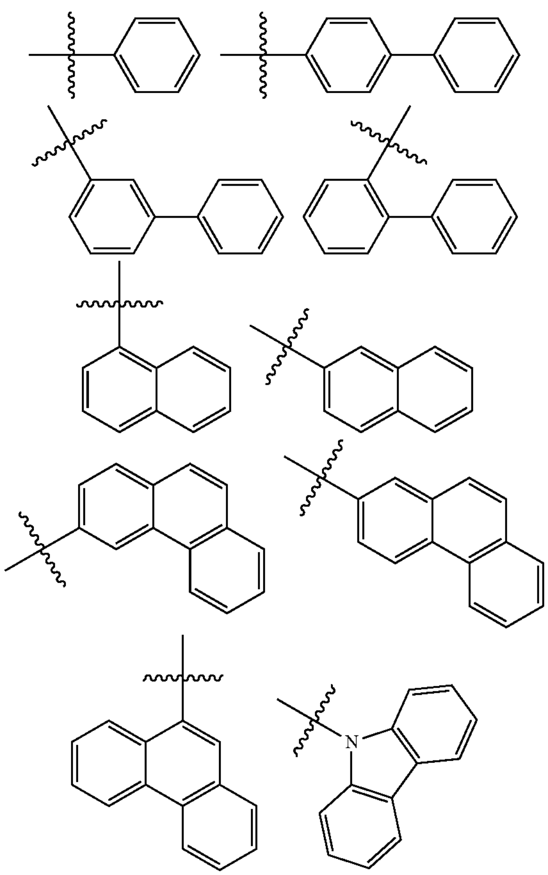

-continued

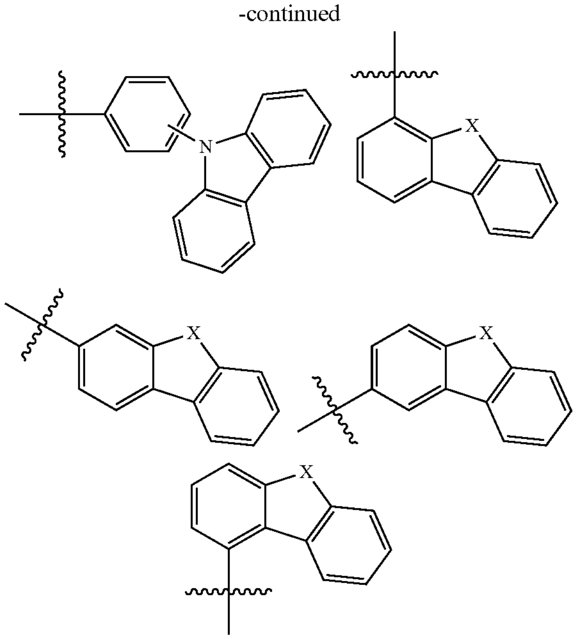

wherein

X may be O, S, N(phenyl), or C(methyl)$_2$.

Preferably, $Ar_1$ and $Ar_2$ may be different from each other.

Preferably, each of $R_1$ and $R_2$ may be phenyl. In this case, n1 representing the number of $R_1$ may be 0 or 1, and n2 representing the number of $R_2$ may be 0, 1, or 2.

Preferably, the compound may be represented by any one of the following Chemical Formulae 1-1 to 1-5:

[Chemical Formula 1-1]

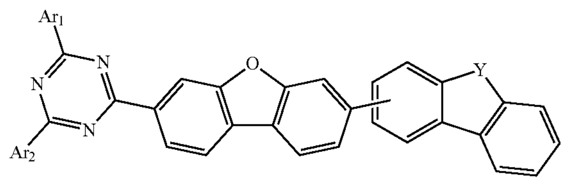

[Chemical Formula 1-2]

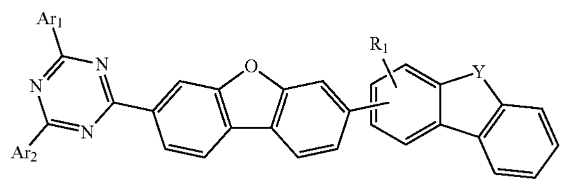

[Chemical Formula 1-3]

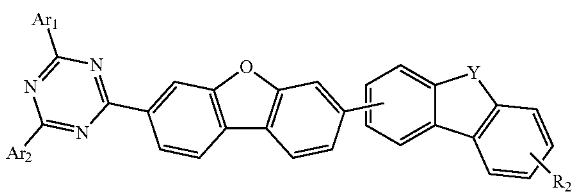

-continued

[Chemical Formula 1-4]

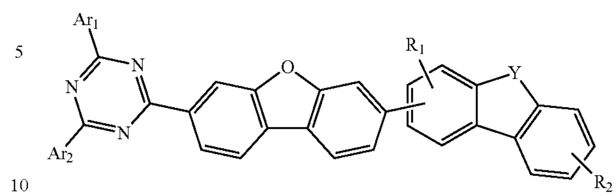

[Chemical Formula 1-5]

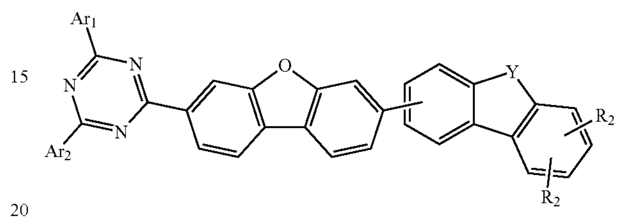

wherein, in Chemical Formulae 1-1 to 1-5,

Y, $Ar_1$, $Ar_2$, $R_1$, and $R_2$ may be the same as those defined in Chemical Formula 1 above, and each substituent $R_2$ in the Chemical Formula 1-5 may be the same as or different from each other.

For example, the above-mentioned compound may be any one selected from the group consisting of the following compounds:

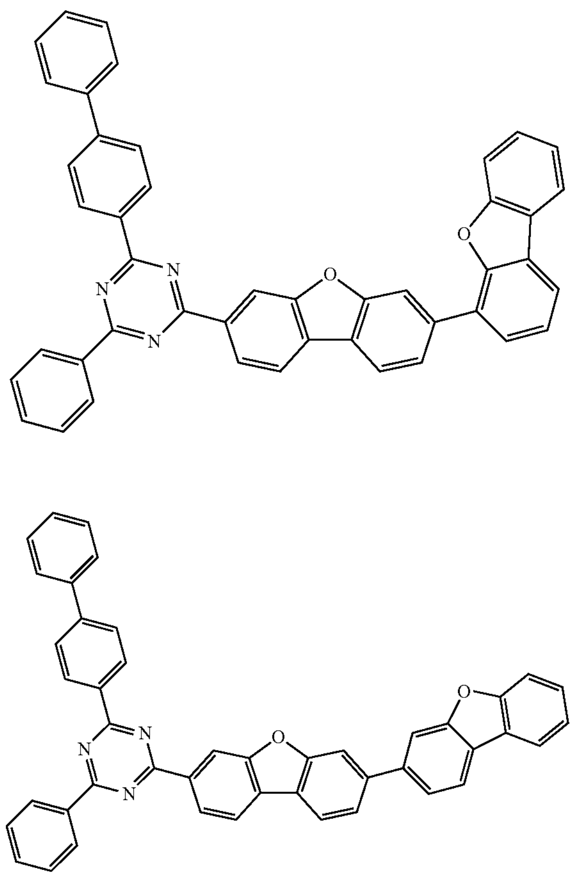

-continued
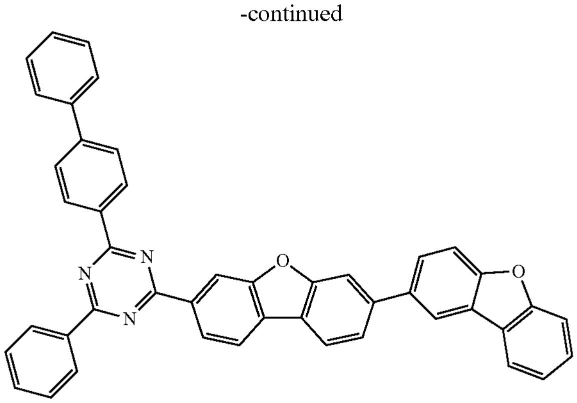
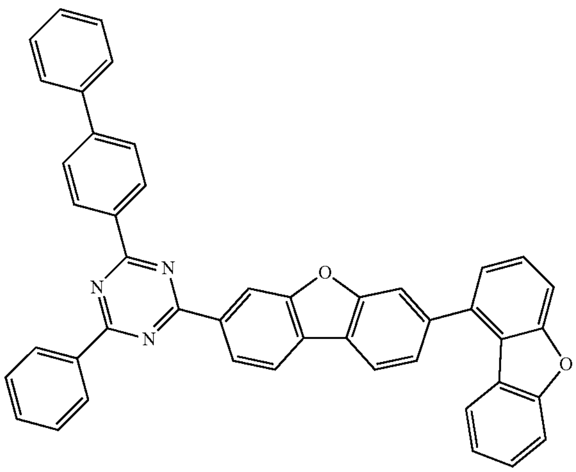
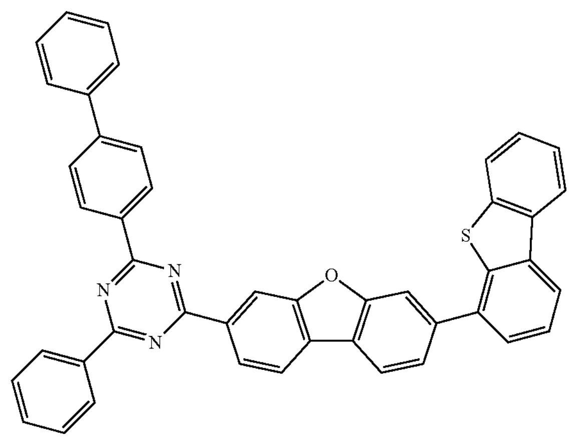
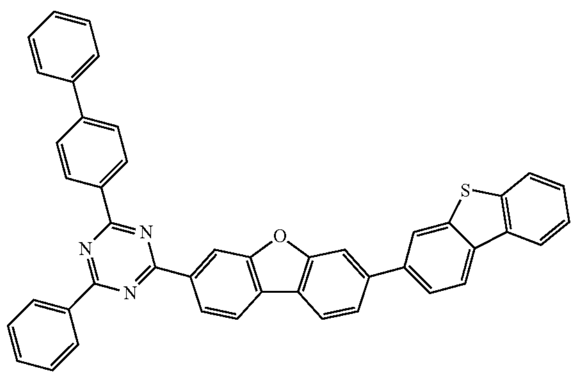
-continued
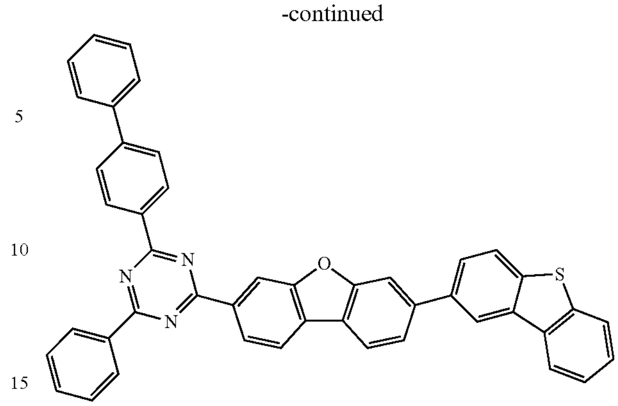
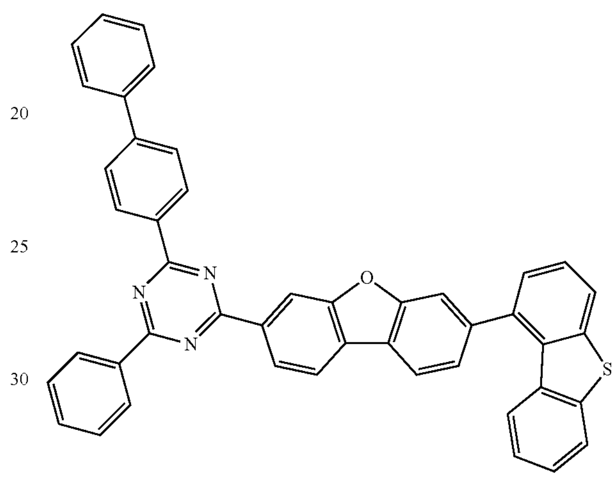
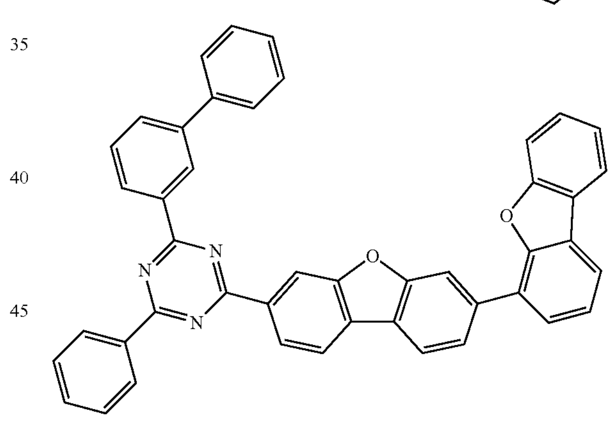
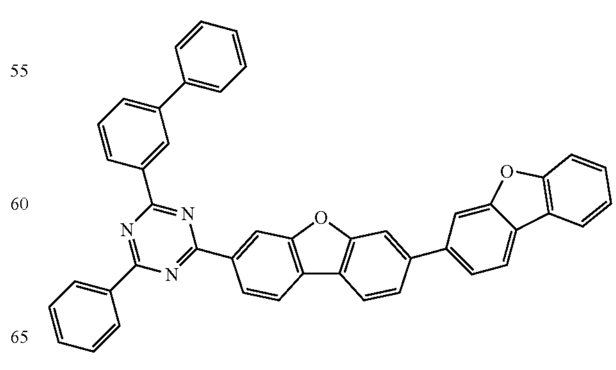

-continued
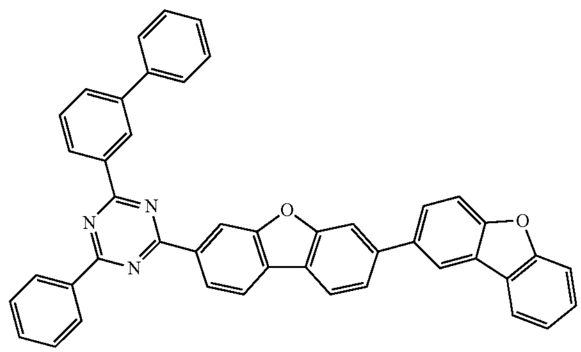
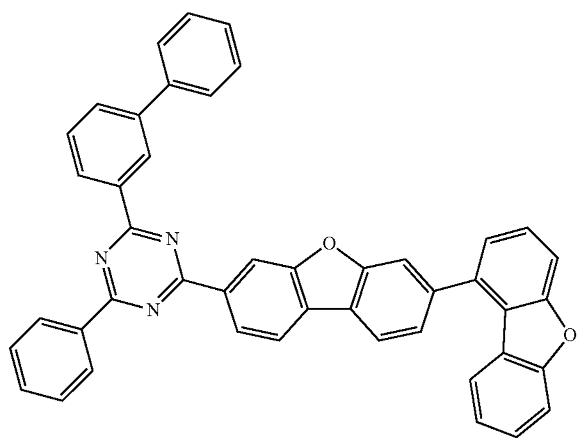
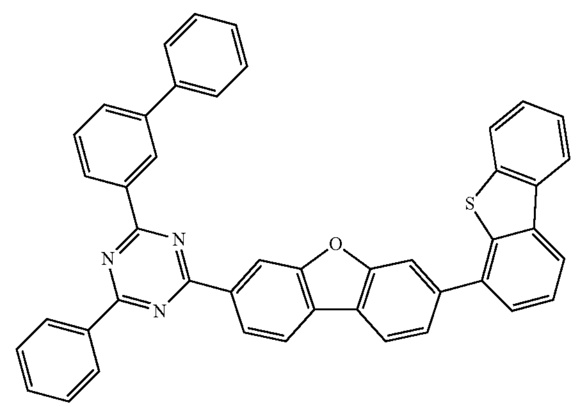
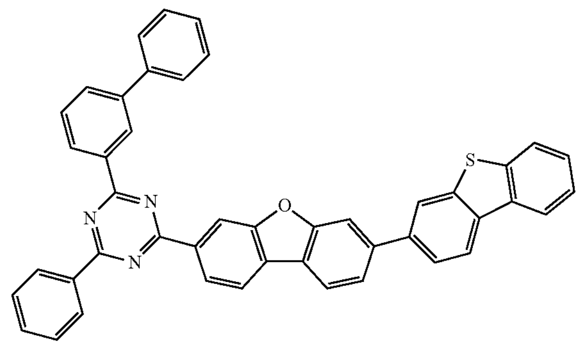
-continued
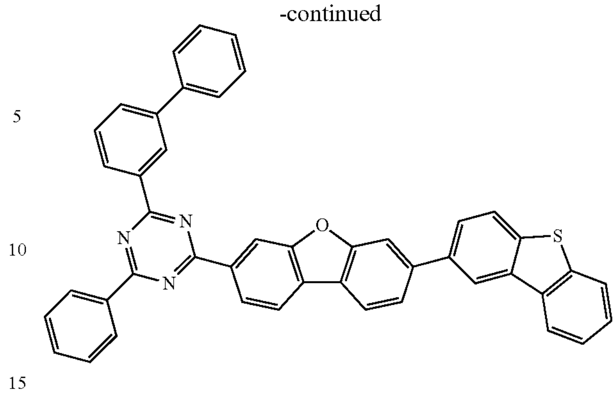
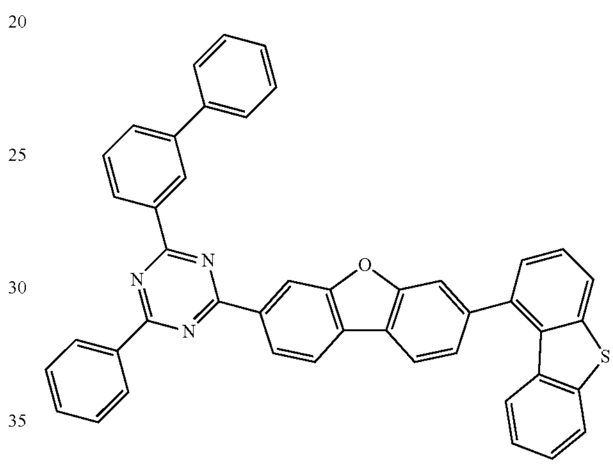
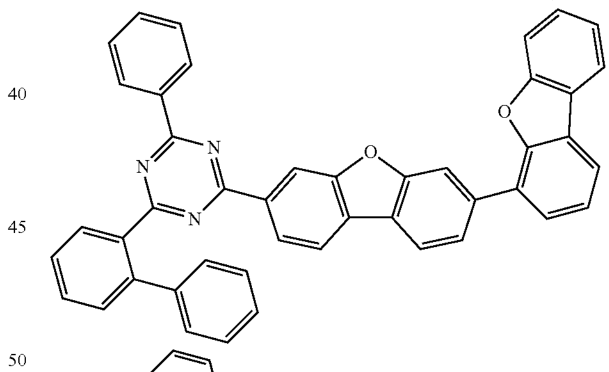
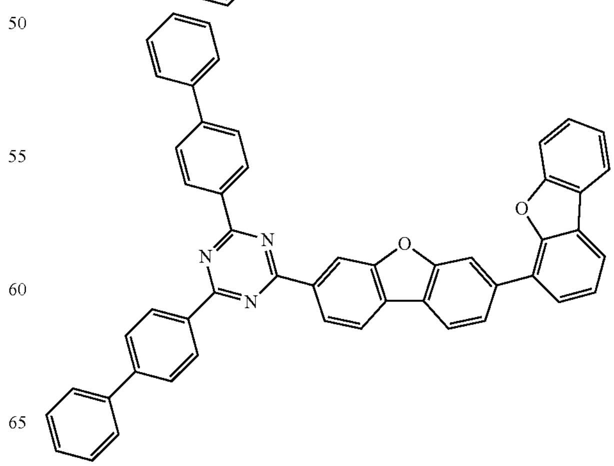

-continued
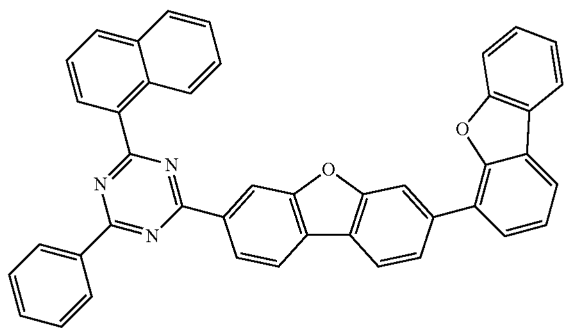
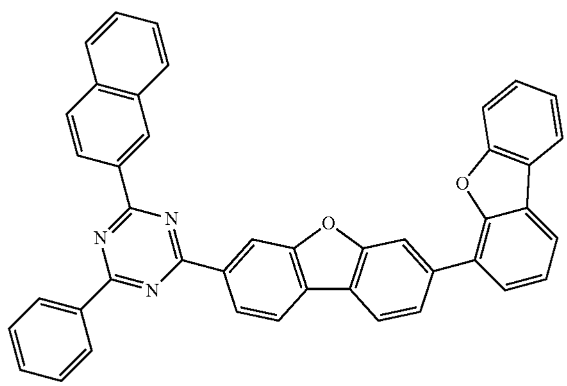
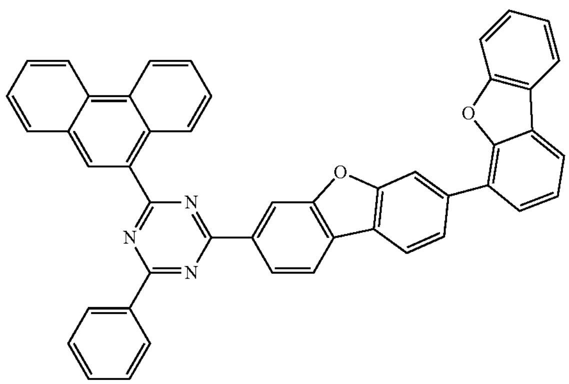
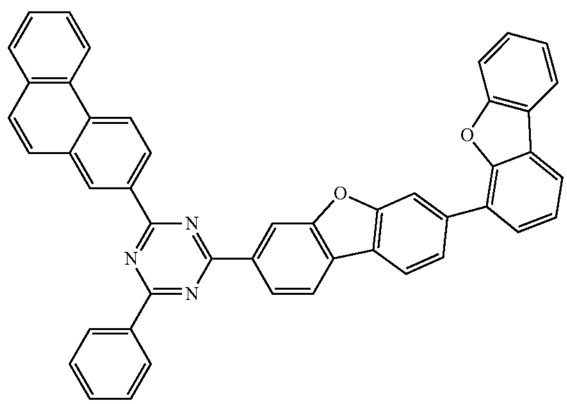
-continued
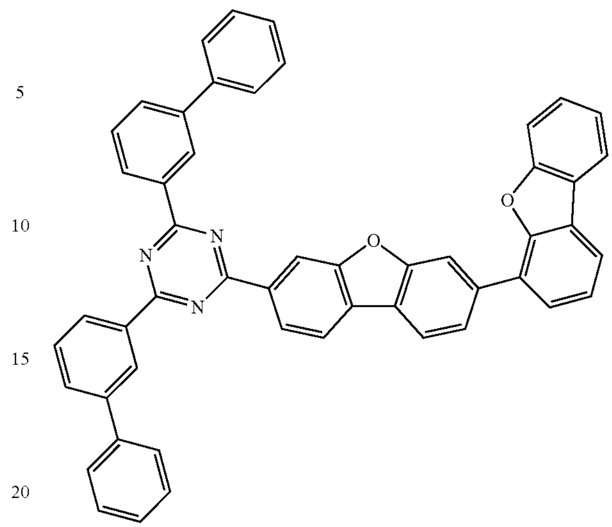
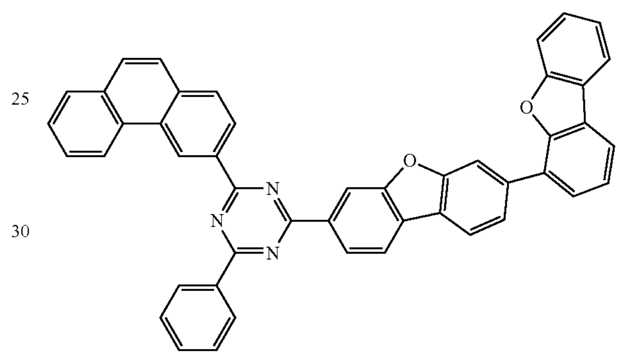
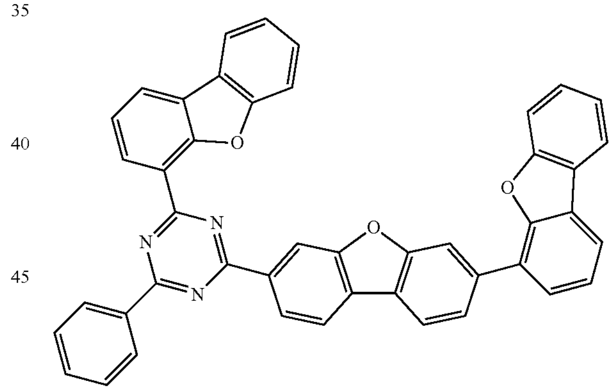
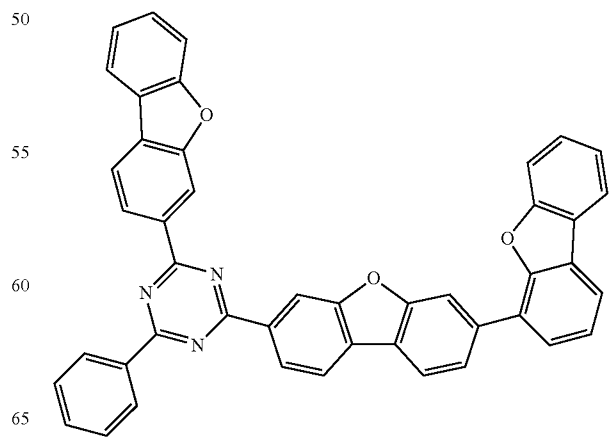

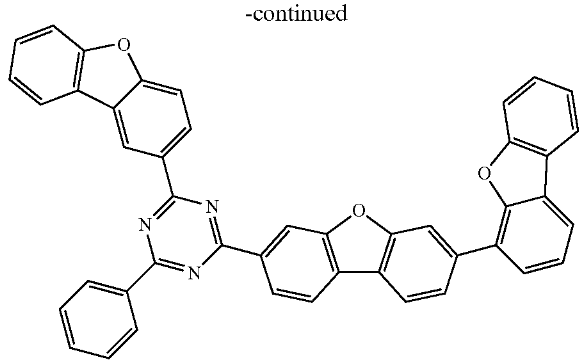
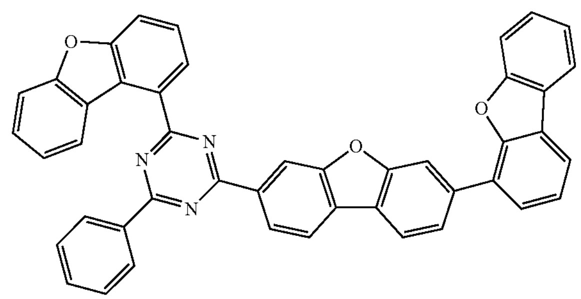
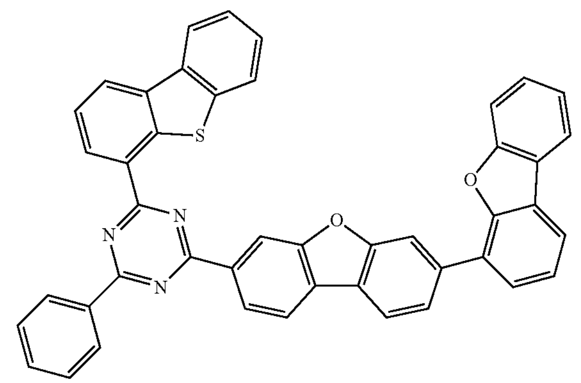
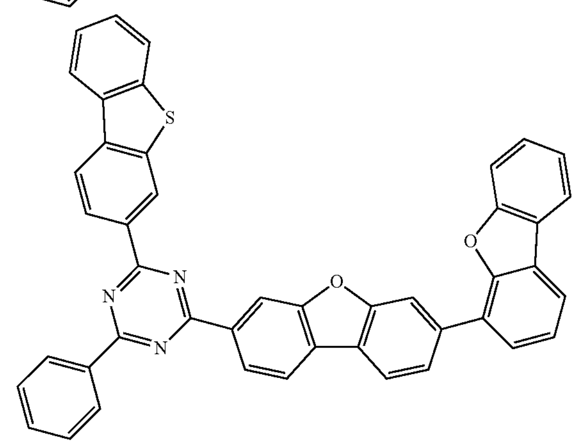
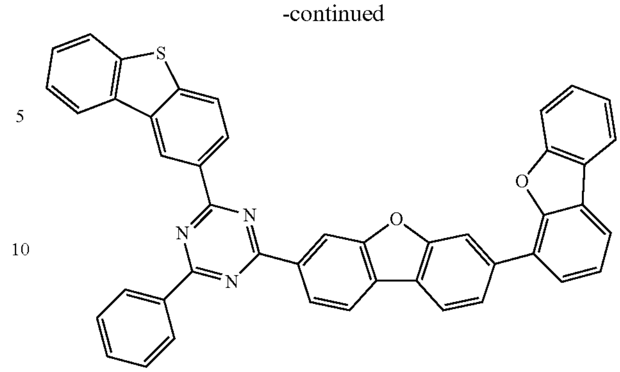
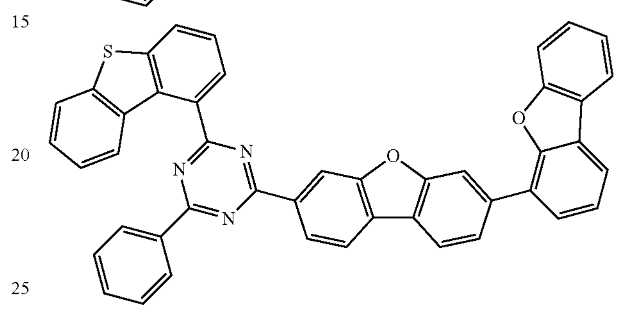
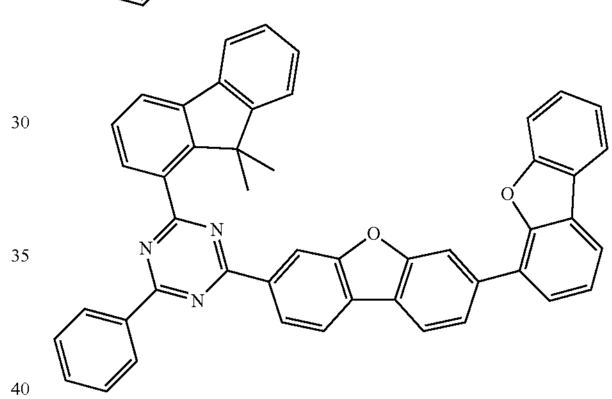
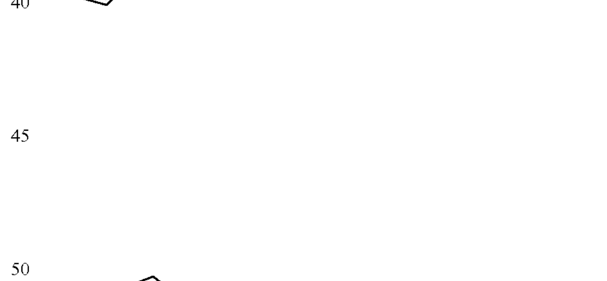
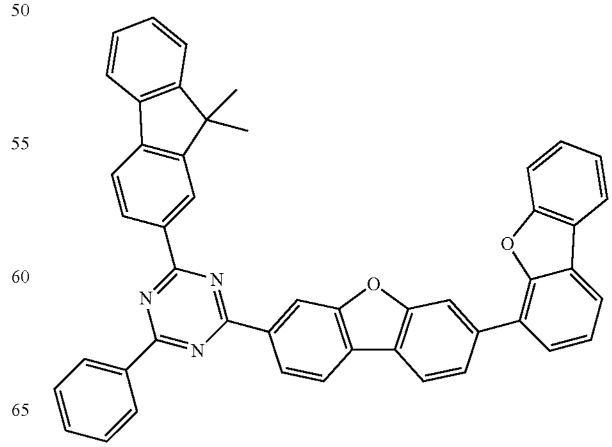

-continued
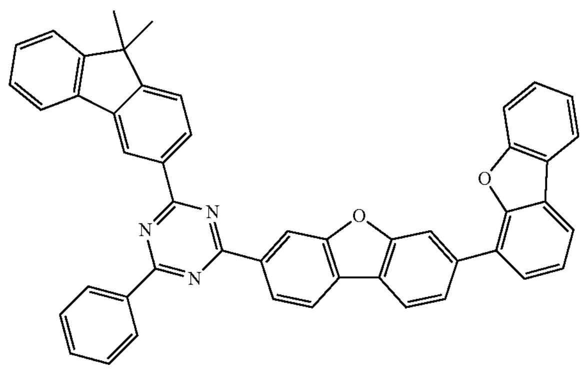
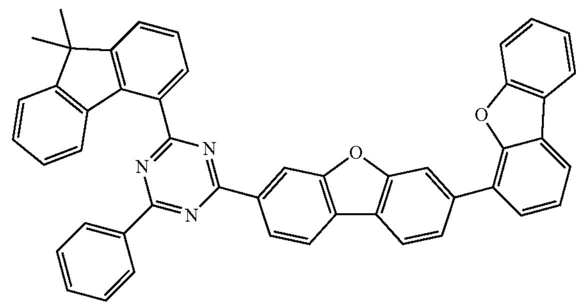
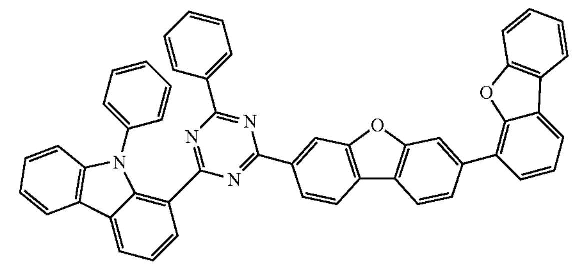
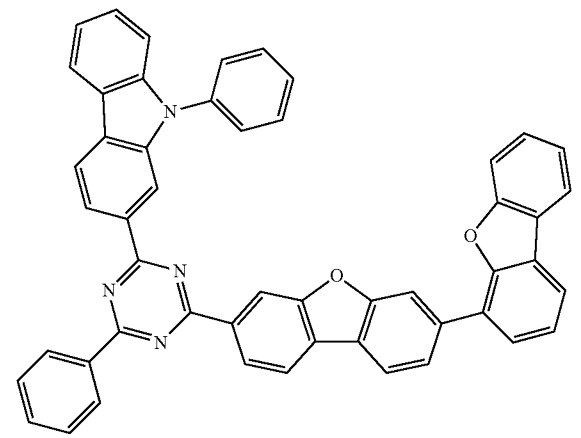
-continued
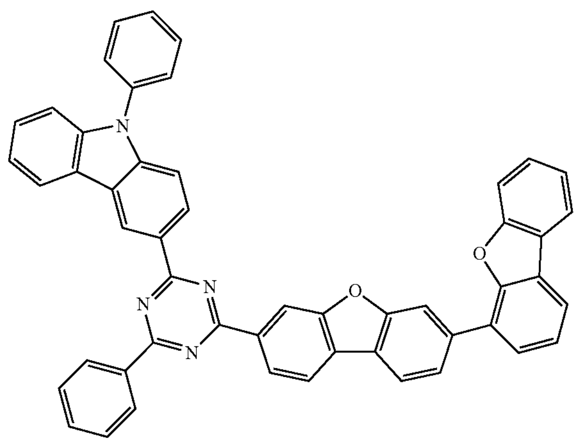
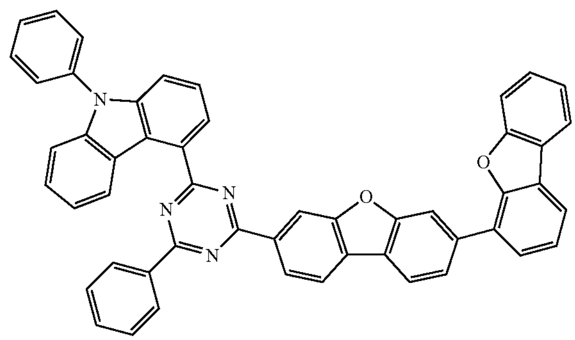
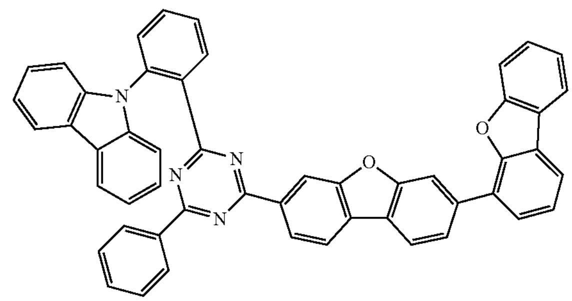
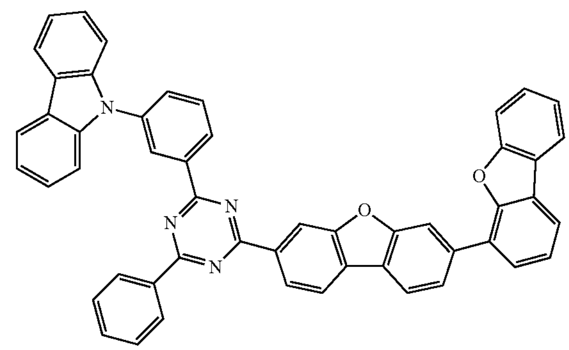

-continued
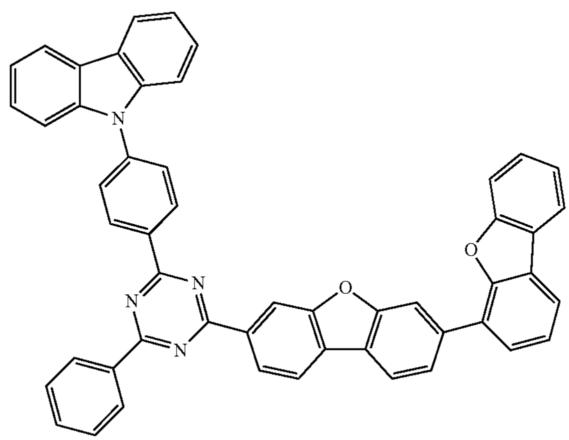
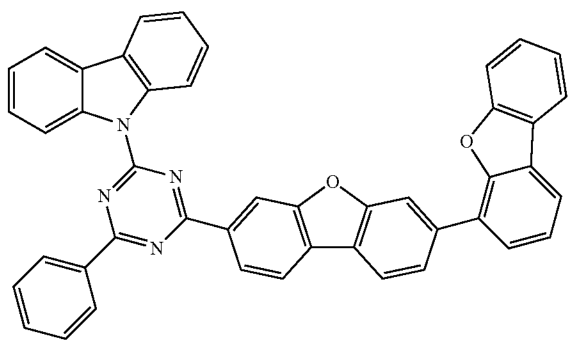
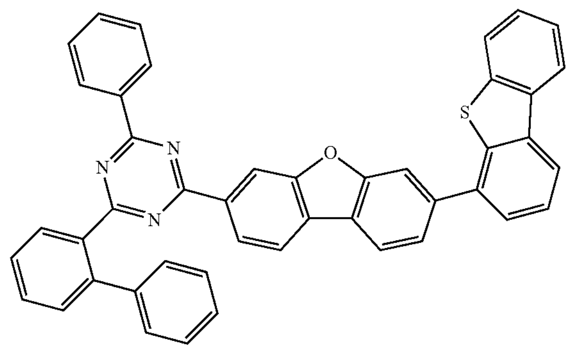
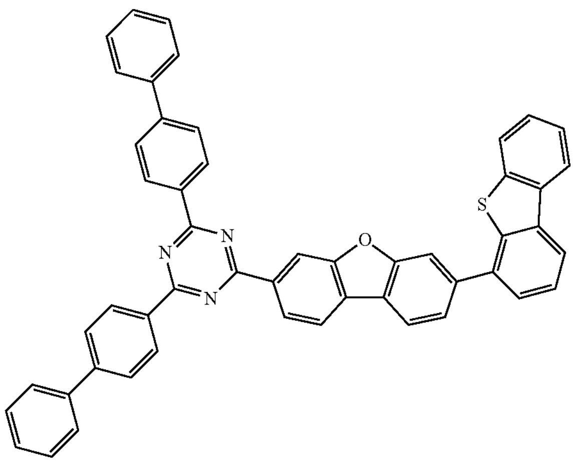
-continued
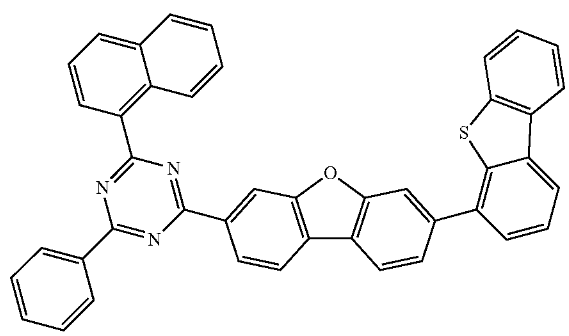
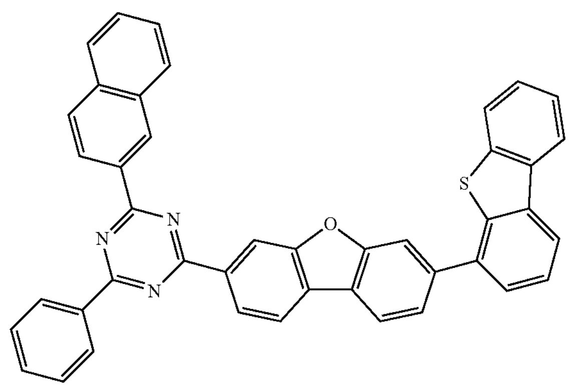
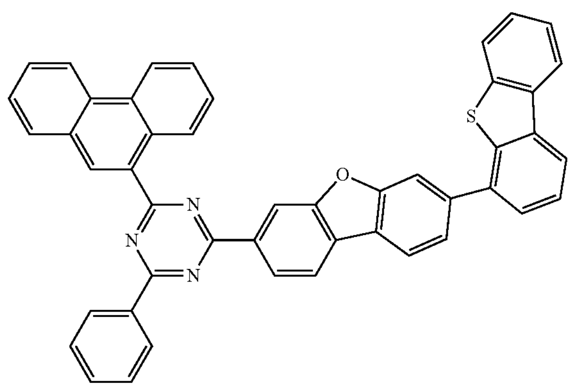
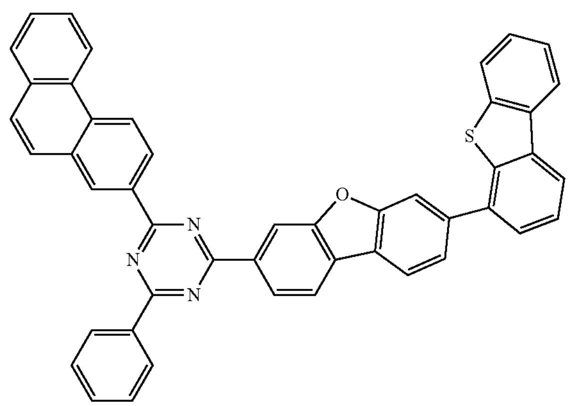

-continued
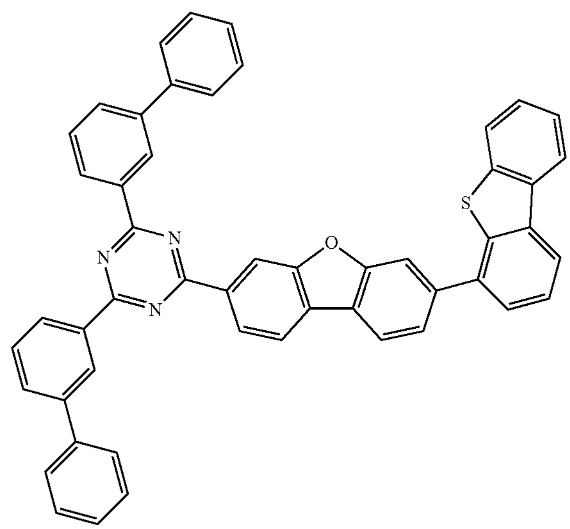
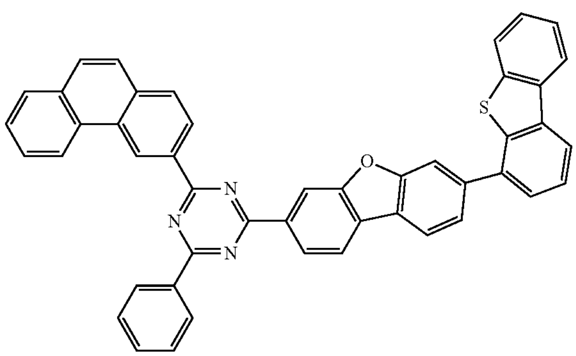
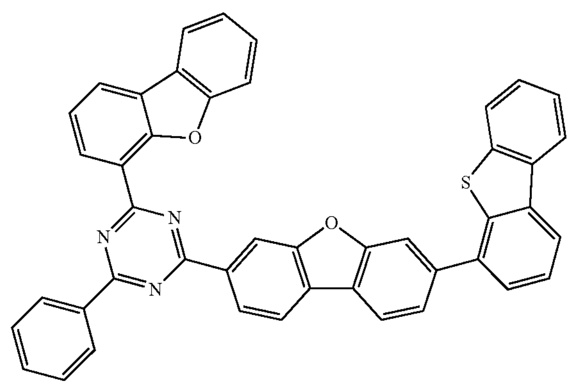
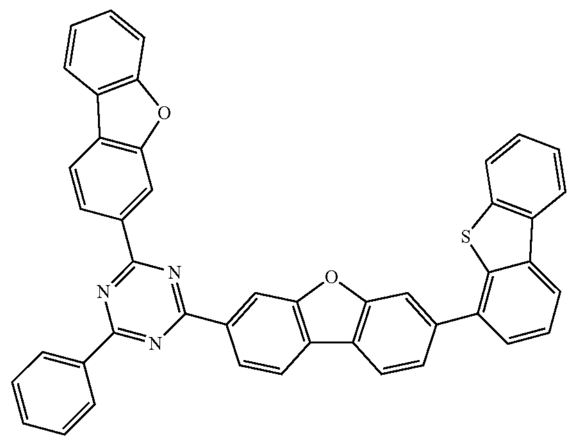
-continued
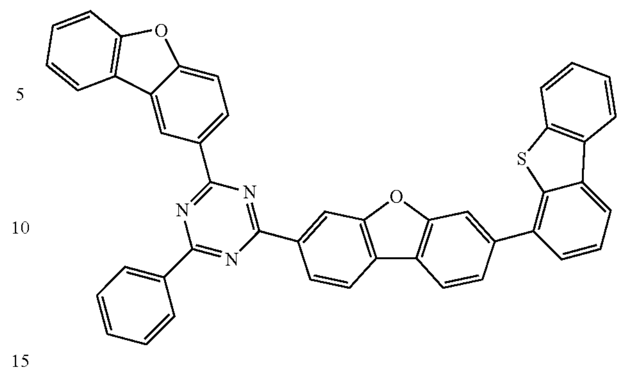
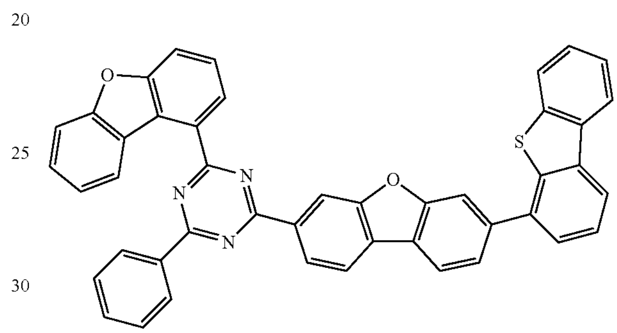
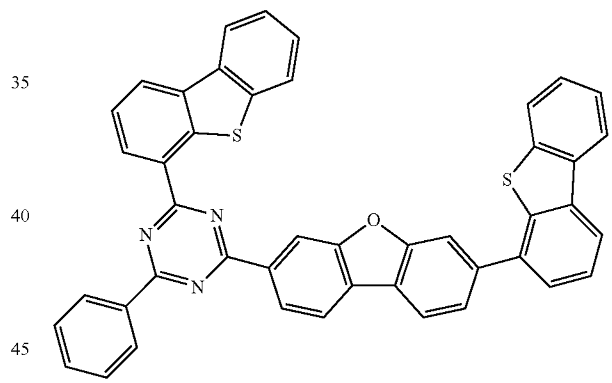
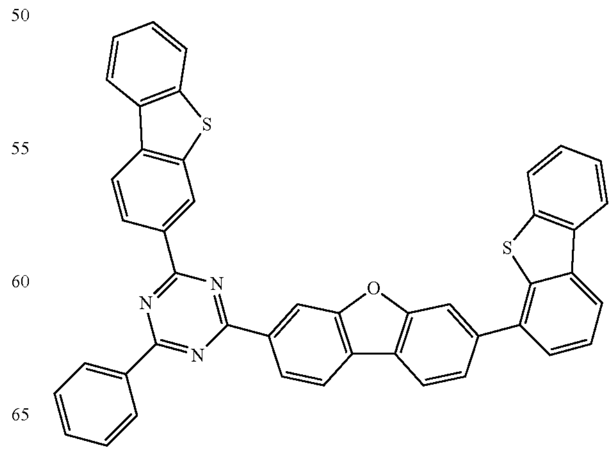

-continued
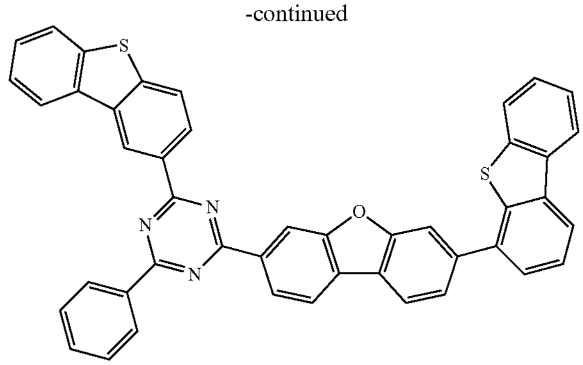
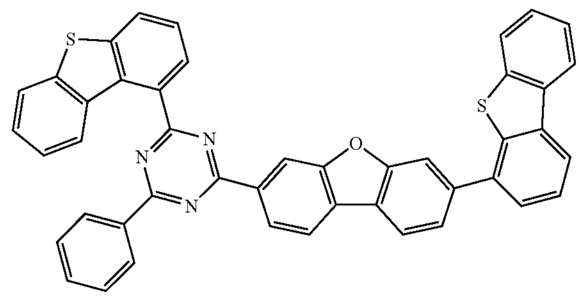
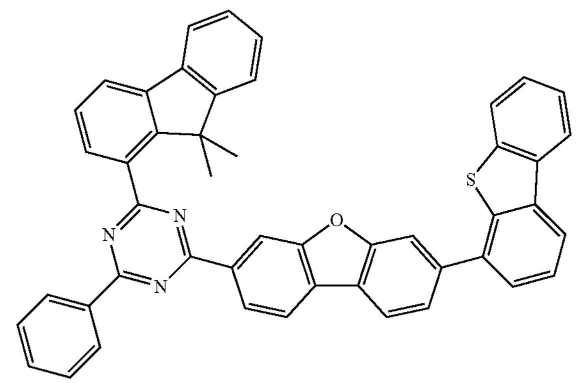
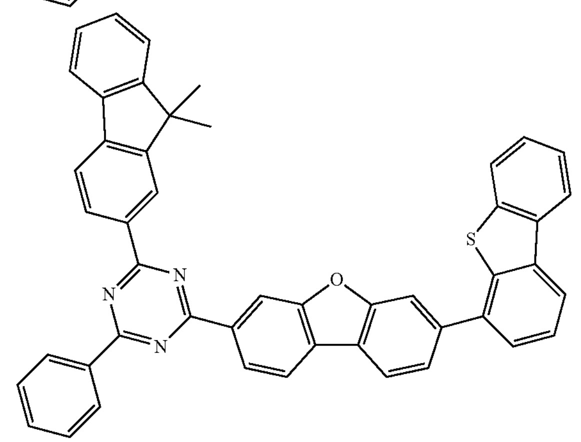
-continued
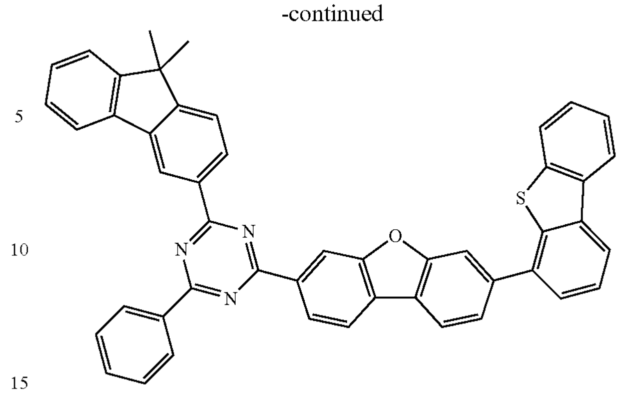
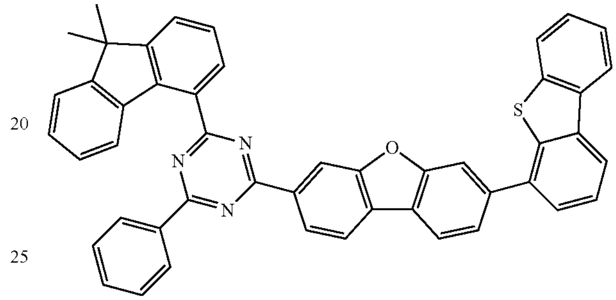
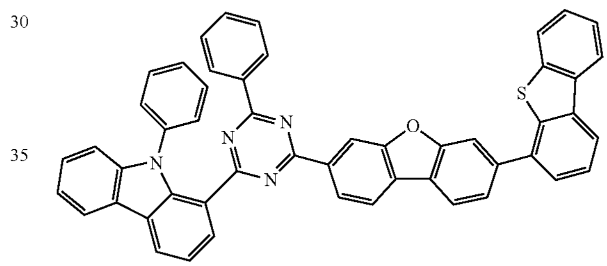
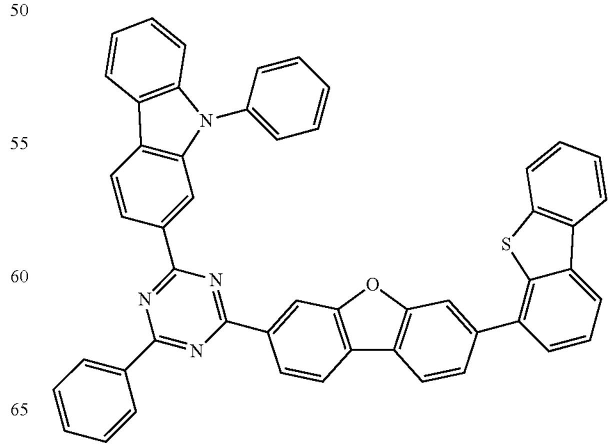

-continued
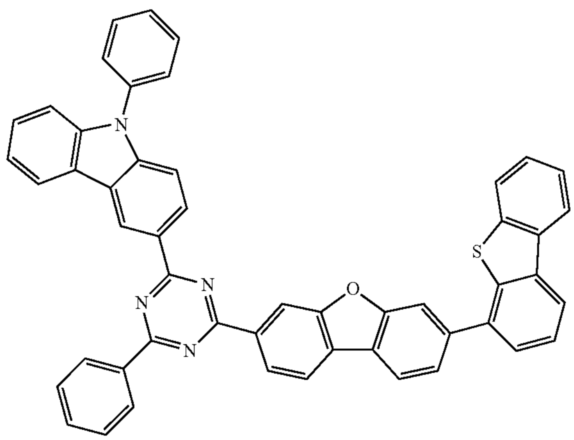
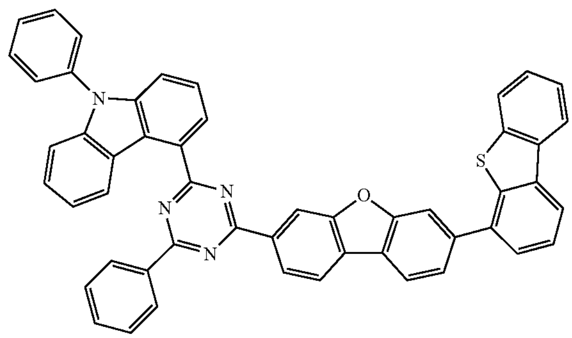
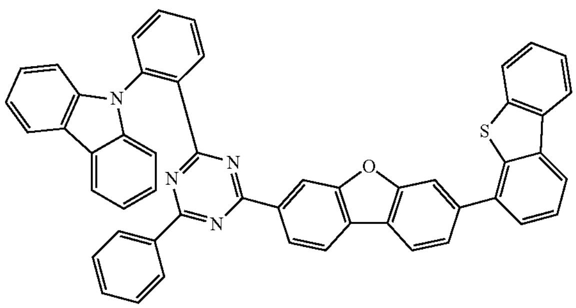
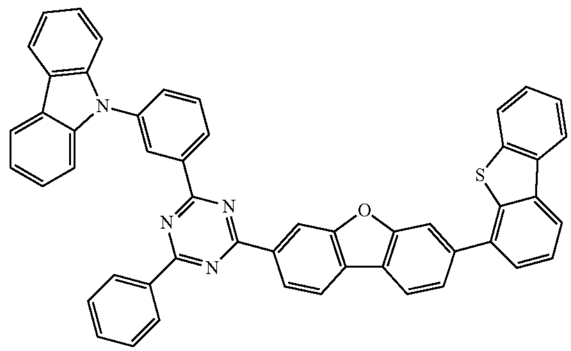
-continued
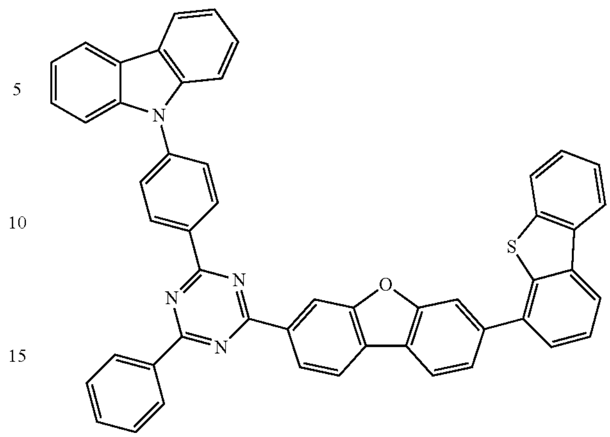
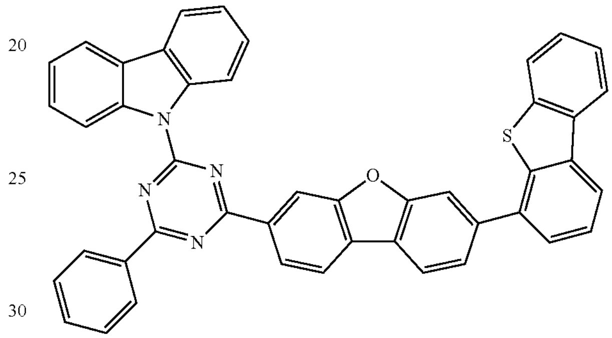
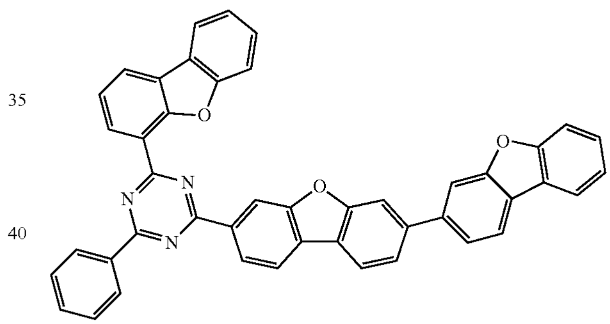
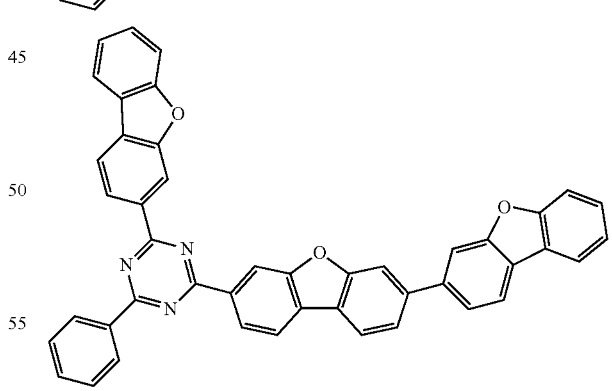

-continued
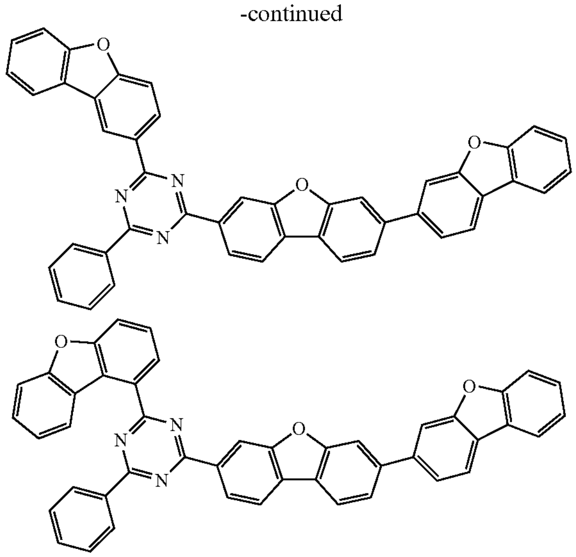
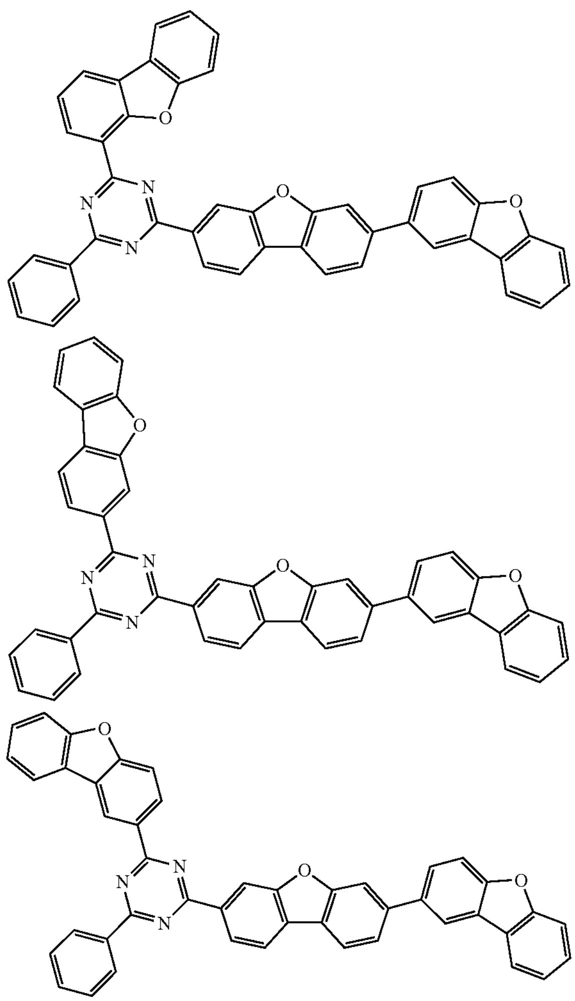
-continued
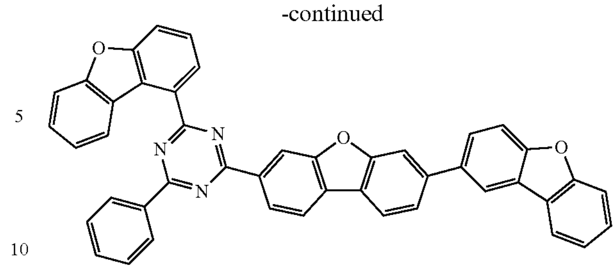
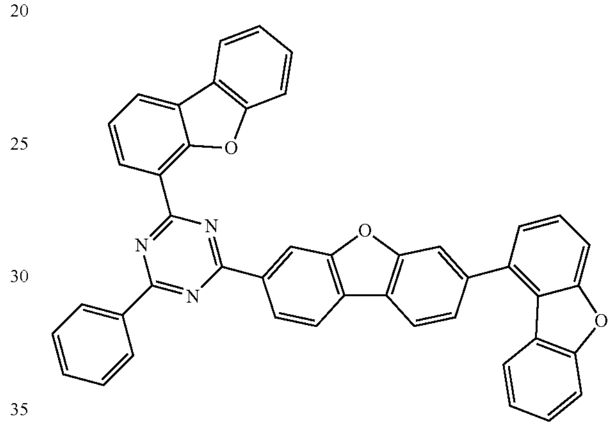
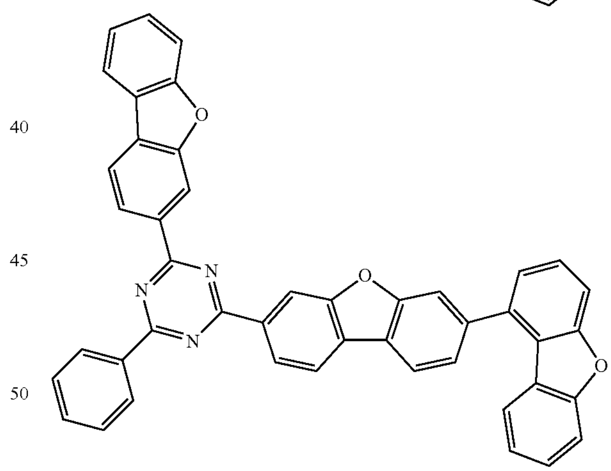
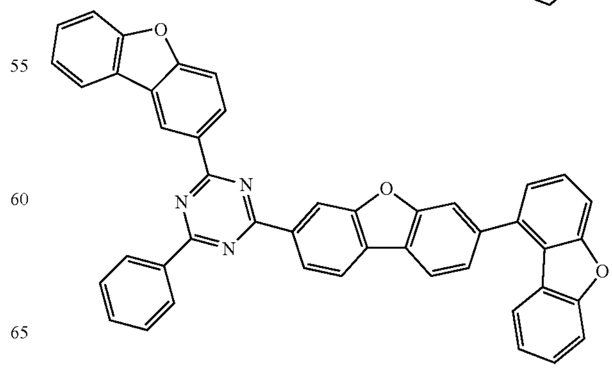

-continued

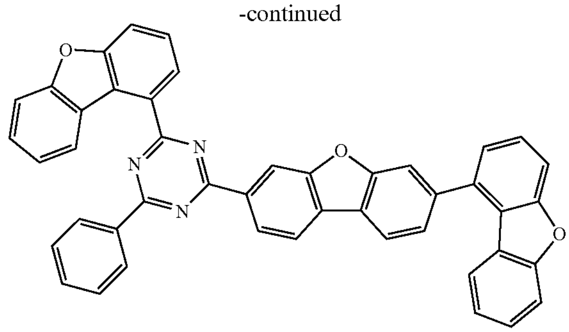

Meanwhile, the compound represented by Chemical Formula 1 can be prepared, for example, according to the preparation method as shown in the following Reaction Scheme 1.

The organic material layer of the organic light emitting device of the present disclosure may have a single layer structure, or it may have a multilayered structure in which two or more organic material layers are stacked. For example, the organic light emitting device of the present disclosure may have a structure including a hole injection layer, a hole transport layer, a light emitting layer, an electron transport layer, an electron injection layer, and the like as the organic material layer. However, the structure of the organic light emitting device is not limited thereto, and it may include a smaller number of organic layers.

Further, the organic material layer may include a light emitting layer, wherein the light emitting layer includes a compound represented by Chemical Formula 1. In particular, the compound according to the present disclosure can be used as a host in a light emitting layer. Specifically, the compound according to the present disclosure can be used as a green phosphorescent host in the light emitting layer.

[Reaction Scheme 1]

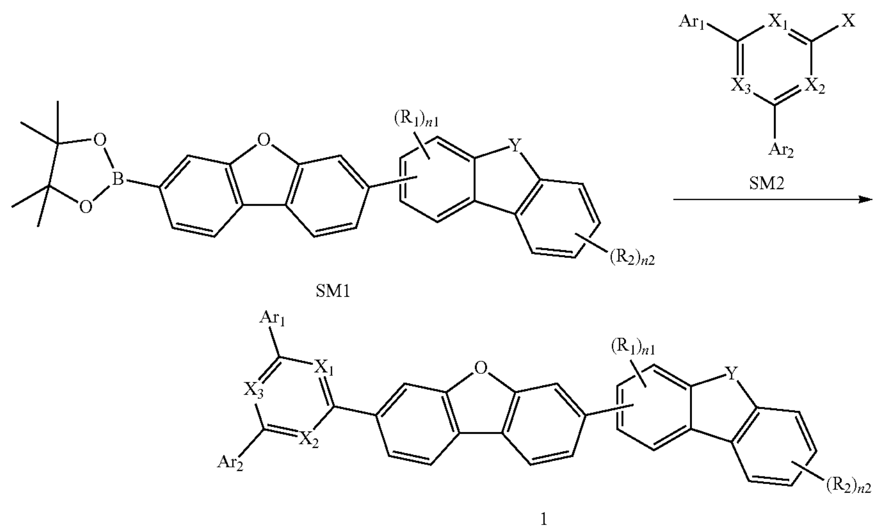

SM2

SM1

1

In Reaction Scheme 1, X is a halogen, preferably bromo or chloro, and the definition of each substituent is as defined above.

Specifically, the compound represented by Chemical Formula 1 is prepared by Suzuki coupling reaction of starting materials SM1 and SM2. At this time, the Suzuki coupling reaction is preferably performed under a palladium catalyst and a base, and the reactive group for the reaction can be modified into a reactive group known in the art. Such a preparation method can be further specified in preparation examples described hereinafter.

Organic Light Emitting Device

In another embodiment of the invention, there is provided an organic light emitting device including the compound represented by Chemical Formula 1 described above. As an example, there is provided an organic light emitting device including: a first electrode; a second electrode provided to face the first electrode; and one or more organic material layers provided between the first electrode and the second electrode, wherein one or more layers of the organic material layers include the compound represented by Chemical Formula 1.

Further, the organic material layer may include an electron transport layer or an electron injection layer, wherein the electron transport layer or the electron injection layer may include a compound represented by Chemical Formula 1.

The organic material layer of the organic light emitting device of the present disclosure may have a single layer structure, or it may have a multilayered structure in which two or more organic material layers are stacked. For example, the organic light emitting device of the present disclosure may have a structure further including a hole injection layer and a hole transport layer provided between the first electrode and the light emitting layer, and an electron transport layer and an electron injection layer provided between the light emitting layer and the second electrode, in addition to the light emitting layer. However, the structure of the organic light emitting device is not limited thereto, and it may include a smaller number of organic layers or a larger number of organic layers.

Further, the organic light emitting device according to the present disclosure may be a normal type of organic light emitting device in which an anode, one or more organic material layers, and a cathode are sequentially stacked on a substrate. In addition, the organic light emitting device according to the present disclosure may be an inverted type of organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound represented by Chemical Formula 1 may be included in the light emitting layer.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4. In such a structure, the compound represented by Chemical Formula 1 may be included in one or more layers of the hole injection layer, the hole transport layer, the light emitting layer, and the electron transport layer. For example, the compound represented by Chemical Formula 1 may be included in the light emitting layer.

The organic light emitting device according to the present disclosure may be manufactured by materials and methods known in the art, except that one or more layers of the organic material layers include the compound represented by Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer, and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer, and an anode material on a substrate.

Further, the compound represented by Chemical Formula 1 may be formed into an organic layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO2003/012890). However, the manufacturing method is not limited thereto.

As an example, the first electrode is an anode and the second electrode is a cathode, or alternatively the first electrode is a cathode and the second electrode is an anode.

As the anode material, generally, a material having a large work function is preferably used so that holes can be smoothly injected into the organic material layer.

Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene] (PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al; and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer refers to a layer that is formed on the hole transport layer and is preferably disposed in contact with the light emitting layer to adjust hole mobility, prevent excessive movement of electrons, and increase the probability of hole-electron bonding, thereby serving to improve the efficiency of an organic light emitting diode. The electron blocking layer includes an electron blocking material, and examples of such electron blocking materials include the compound represented by Chemical Formula 1, or arylamine-based organic materials and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex ($Alq_3$); a carbazole-based compound; a dimerized styryl compound; BAlq; a 10-hydroxybenzoquinoline-metal compound; a benzoxazole-, benzothiazole-, and benzimidazole-based compound; a poly(p-phenylene vinylene) (PPV)-based polymer; a spiro compound; polyfluorene, rubrene, and the like; but are not limited thereto.

The light emitting layer may include a host material and a dopant material as described above.

The light emitting layer may include the compound represented by Chemical Formula 1 as the host material.

Alternatively, the light emitting layer may include two or more kinds of hosts, wherein one of the hosts may be a compound represented by Chemical Formula 1. A host material that can be used in addition to the compound represented by Chemical Formula 1 may include a fused aromatic ring derivative, a heterocyclic-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has large mobility for electrons. Specific examples thereof include: an Al complex of 8-hydroxyquinoline; a complex including $Alq_3$; an organic radical compound; a hydroxyflavone-metal complex; and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film.

Specific examples thereof may include LiF, NaF, NaCl, CsF, $Li_2O$, BaO, fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front emission type, a back emission type, or a double side emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples.

However, these examples are presented for illustrative purposes only, and are not intended to limit the scope of the present disclosure.

Preparation Example A: Preparation of Intermediate Compound R-4

1) Preparation of Compound R-1

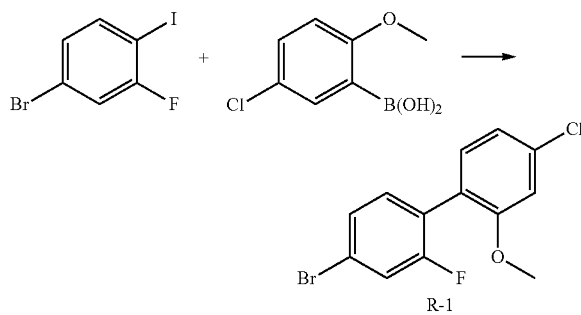

R-1

1-bromo-3-fluoro-4-iodobenzene (50 g, 166.6 mmol) and (5-chloro-2-methoxyphenyl) boronic acid (31.1 g, 166.6 mmol) were dissolved in 800 ml of tetrahydrofuran (THF). A 2 M sodium carbonate ($Na_2CO_3$) solution (250 mL) and tetrakis(triphenylphosphine)palladium(0) [$Pd(PPh_3)_4$] (3.8 g, 3 mol %) were added thereto and refluxed for 12 hours. After the reaction was completed, the mixture was cooled to room temperature, and the resulting mixture was extracted three times with water and toluene. After separating the toluene layer and drying with magnesium sulfate, the filtrate was distilled under reduced pressure, and the mixture obtained was recrystallized three times using chloroform and ethanol to obtain compound R-1 (29.7 g, yield 55%).

MS: $[M+H]^+=314$

2) Preparation of Compound R-2

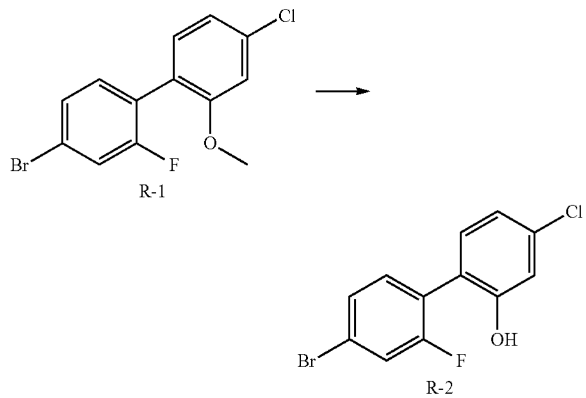

R-1

R-2

Compound R-1 (25.0 g, 150 mmol) prepared in the above step was dissolved in dichloromethane (300 ml) and cooled to 0° C. Boron tribromide (7.9 ml, 83.2 mmol) was slowly added dropwise thereto and stirred for 12 hours. After the reaction was completed, the mixture was washed three times with water, dried over magnesium sulfate, and a filtered filtrate was distilled under reduced pressure and purified by column chromatography to obtain compound R-2 (23.7 g, yield 99%).

MS: $[M+H]^+=300$

3) Preparation of Compound R-3

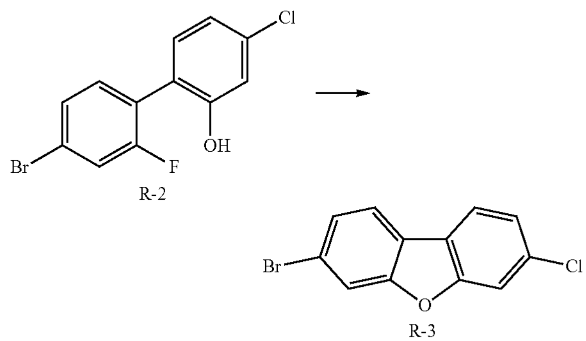

R-2

R-3

Compound R-2 (20.0 g, 66.4 mmol) prepared in the above step was dissolved in distilled dimethylformamide (DMF) (200 ml). It was cooled to 0° C., and sodium hydride (1.8 g, 72.9 mmol) was slowly added dropwise thereto. After stirring for 20 minutes, the mixture was stirred at 100° C. for 1 hour. After the reaction was completed, the mixture was cooled to room temperature, and 100 ml of ethanol was slowly added thereto. The mixture obtained by distilling the above mixture under reduced pressure was recrystallized by chloroform and ethyl acetate to obtain compound R-3 (16.9 g, yield 91%).

MS: $[M+H]^+=280$

4) Preparation of Compound R-4

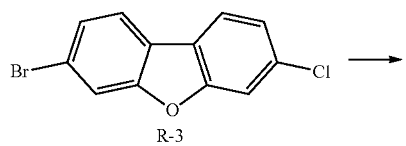

R-3

-continued

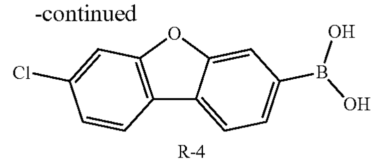

R-4

After dissolving compound R-3 (15.0 g, 53.3 mmol) prepared in the above step in tetrahydrofuran (150 ml), the temperature was lowered to −78° C. and 1.7 M tertiary-butyllithium (t-BuLi) (31.8 ml, 53.3 mmol) was added slowly thereto. After stirring at the same temperature for 1 hour, triisopropyl borate ($B(OiPr_3)$) (14.2 ml, 107.0 mmol) was added thereto, and the mixture was stirred for 3 hours while gradually raising the temperature to room temperature. To the reaction mixture, 2 N aqueous hydrochloric acid (100 ml) was added and stirred at room temperature for 1.5 hours. The resulting precipitate was filtered, washed sequentially with water and ethyl ether, and then dried under vacuum.

After drying, it was dispersed in ethyl ether, stirred for 2 hours, filtered and dried to prepare compound R-4 (12.5 g, yield 95%).

MS: $[M+H]^+=247$

Preparation Example B: Preparation of Intermediate Compound Sub 1-2

1) Preparation of Compound Sub 1-1

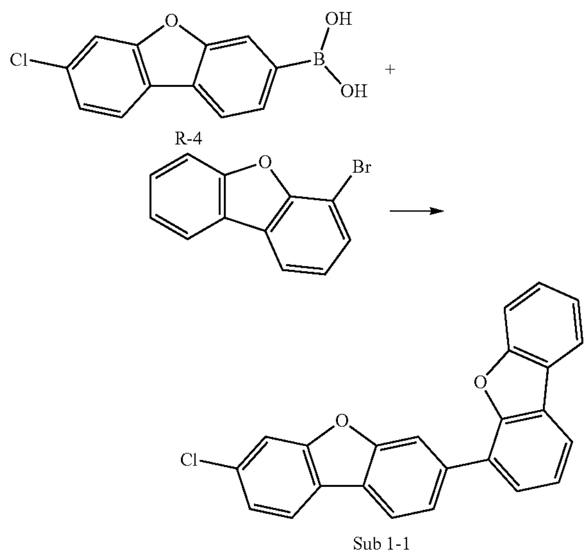

R-4

Sub 1-1

Under a nitrogen atmosphere, R-4 (20 g, 81.3 mmol) prepared in Preparation Example A and 4-bromodibenzo[b,d]furan (20 g, 81.3 mmol) were added to 400 ml of tetrahydrofuran, which were stirred and refluxed. Subsequently, potassium carbonate (33.7 g, 243.9 mmol) was dissolved in 34 ml of water, and added, stirred thoroughly, and then tetrakis(triphenylphosphine)palladium(0) $[Pd(PPh_3)_4]$ (2.8 g, 2.4 mmol) was added thereto. After the reaction for 3 hours, and after cooling to room temperature, the organic layer and the water layer were separated and the organic layer was distilled. The distillate was again dissolved in 598 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound Sub 1-1 (20.0 g, 67%).

MS: $[M+H]^+$=369.1

2) Preparation of Compound Sub 1-2

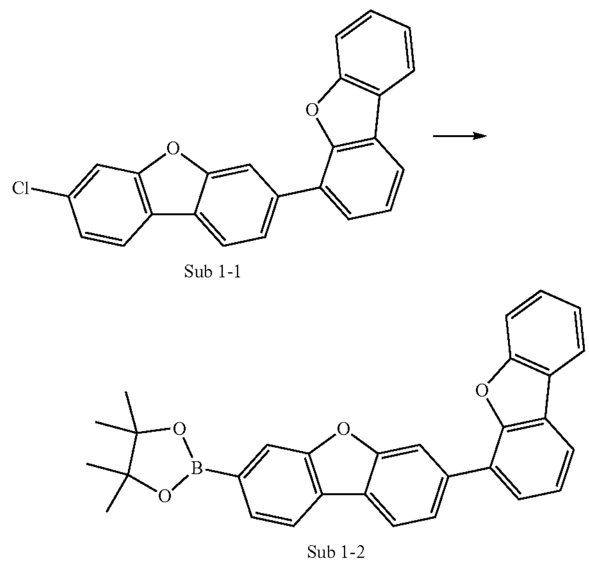

Sub 1-1

Sub 1-2

Under a nitrogen atmosphere, Sub 1-1 (15 g, 40.8 mmol) prepared in the above step and bis(pinacolato)diboron (20.7 g, 81.5 mmol) were added to 300 ml of 1,4-dioxane (Diox), which were stirred and refluxed. After that, potassium acetate (11.8 g, 122.3 mmol) was added and stirred sufficiently, followed by bis(dibenzylideneacetone)palladium (0.7 g, 1.2 mmol) and tricyclohexylphosphine (0.7 g, 2.4 mmol). After the reaction for 5 hours, and after cooling to room temperature, the organic layer was filtered to remove a salt, and then the filtered organic layer was distilled. The distillate was again dissolved in 188 mL of chloroform, washed twice with water, and the organic layer was separated. After adding anhydrous magnesium sulfate and stirring, the filtrate was distilled under reduced pressure. The concentrated compound was recrystallized by chloroform and ethanol to prepare a white solid compound Sub 1-2 (14.5 g, 77%).

MS: $[M+H]^+$=461.2

Preparation Example C: Preparation of Intermediate Compound Sub 2-2

1) Preparation of Compound Sub 2-1

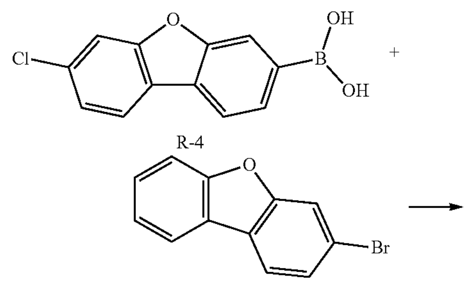

R-4

-continued

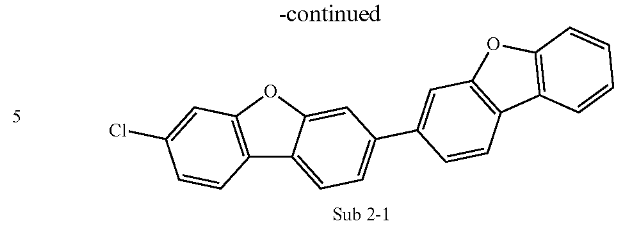

Sub 2-1

Under a nitrogen atmosphere, R-4 (20 g, 81.3 mmol) prepared in Preparation Example A and 3-bromodibenzo[b, d]furan (20 g, 81.3 mmol) were added to 400 ml of tetrahydrofuran, which were stirred and refluxed. Subsequently, potassium carbonate (33.7 g, 243.9 mmol) was dissolved in 34 ml of water, and added, stirred thoroughly, and then tetrakis(triphenylphosphine)palladium(0) [$Pd(PPh_3)_4$] (2.8 g, 2.4 mmol) was added thereto. After the reaction for 3 hours, and after cooling to room temperature, the organic layer and the water layer were separated and the organic layer was distilled. The distillate was again dissolved in 598 ml of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound Sub 2-1 (21 g, 70%).

MS: $[M+H]^+$=369.1

2) Preparation of Compound Sub 2-2

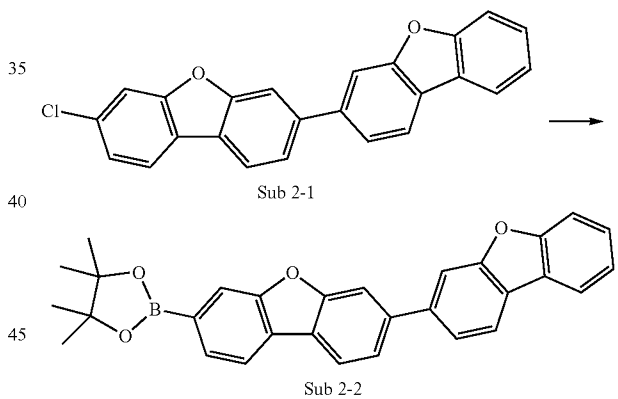

Sub 2-1

Sub 2-2

Under a nitrogen atmosphere, Sub 2-1 (15 g, 28.2 mmol) prepared in the above step and bis(pinacolato)diboron (14.4 g, 56.5 mmol) were added to 300 ml of 1,4-dioxane (Diox), which were stirred and refluxed. After that, potassium acetate (8.1 g, 84.7 mmol) was added thereto and stirred sufficiently, and then bis(dibenzylideneacetone)palladium (0.5 g, 0.8 mmol) and tricyclohexylphosphine (0.5 g, 1.7 mmol) were added thereto. After the reaction for 5 hours, and after cooling to room temperature, the organic layer was filtered to remove a salt, and then the filtered organic layer was distilled. The distillate was again dissolved in 130 ml of chloroform, washed twice with water, and the organic layer was separated. After adding anhydrous magnesium sulfate and stirring, the filtrate was distilled under reduced pressure. The concentrated compound was recrystallized by chloroform and ethanol to prepare a white solid compound Sub 2-2 (10.1 g, 78%).

MS: $[M+H]^+$=461.2

Preparation Example D: Preparation of Intermediate Compound Sub 3-2

1) Preparation of Compound Sub 3-1

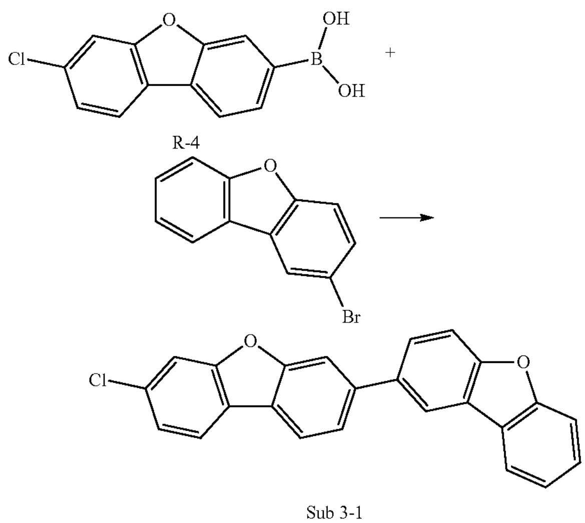
R-4

Sub 3-1

Under a nitrogen atmosphere, nitrogen R-4 (20 g, 81.3 mmol) prepared in Preparation Example A and 2-bromodibenzo[b,d]furan (20 g, 81.3 mmol) were added to 400 ml of tetrahydrofuran, which were stirred and refluxed. After that, potassium carbonate (33.7 g, 243.9 mmol) was dissolved in 34 ml of water and added, stirred thoroughly, and then tetrakis(triphenylphosphine)palladium(0) [$Pd(PPh_3)_4$] (2.8 g, 2.4 mmol) was added thereto. After the reaction for 2 hours, and after cooling to room temperature, the organic layer and the water layer were separated and the organic layer was distilled. The distillate was again dissolved in 598 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound Sub 3-1 (19.8 g, 66%).

MS: $[M+H]^+$=369.1

2) Preparation of Compound Sub 3-2

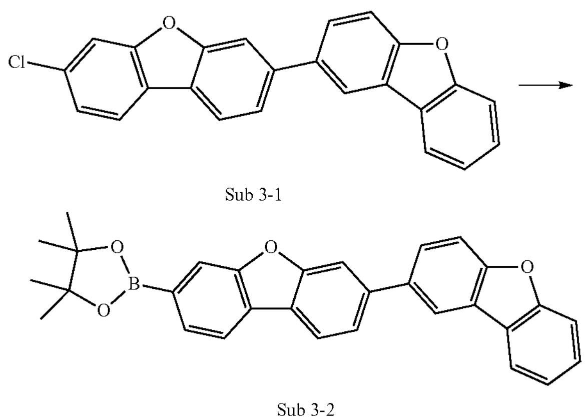
Sub 3-1

Sub 3-2

Under a nitrogen atmosphere, Sub 3-1 (15 g, 37.5 mmol) and bis(pinacolato)diboron (19.1 g, 75 mmol) prepared in the above step were placed in 300 ml of 1,4-dioxane, which were stirred and refluxed. After that, potassium acetate (10.8 g, 112.5 mmol) was added and stirred sufficiently, followed by bis(dibenzylideneacetone)palladium (0.6 g, 1.1 mmol) and tricyclohexylphosphine (0.6 g, 2.3 mmol). After 7 hours of reaction, and after cooling to room temperature, the organic layer was filtered to remove a salt, and then the filtered organic layer was distilled. The distillate was again dissolved in 173 mL of chloroform, washed twice with water, and the organic layer was separated. After adding anhydrous magnesium sulfate and stirring, the filtrate was distilled under reduced pressure. The concentrated compound was recrystallized by chloroform and ethanol to prepare a white solid compound Sub 3-2 (11.6 g, 67%).

MS: $[M+H]^+$=461.2

Preparation Example E: Preparation of Intermediate Compound Sub 4-2

1) Preparation of Compound Sub 4-1

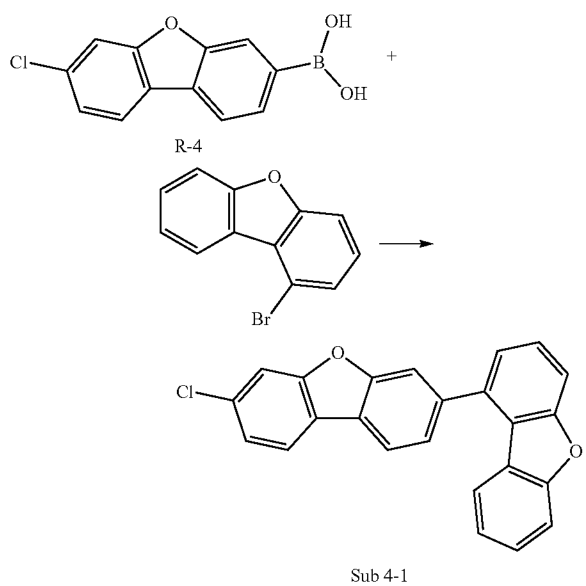
R-4

Sub 4-1

Under a nitrogen atmosphere, R-4 (20 g, 81.3 mmol) prepared in Preparation Example A and 1-bromodibenzo[b,d]furan (20 g, 81.3 mmol) were added to 400 ml of tetrahydrofuran, which were stirred and refluxed. After that, potassium carbonate (33.7 g, 243.9 mmol) was dissolved in 34 ml of water, and added, stirred thoroughly, and then tetrakis(triphenylphosphine)palladium(0) [$Pd(PPh_3)_4$] (2.8 g, 2.4 mmol) was added. After the reaction for 2 hours, and after cooling to room temperature, the organic layer and the water layer were separated and the organic layer was distilled. The distillate was again dissolved in 598 ml of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound Sub 4-1 (20.3 g, 68%).

MS: [M H]=369.1

2) Preparation of Compound Sub 4-2

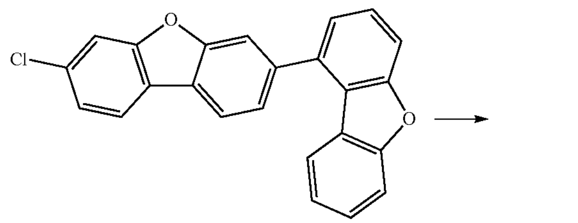

Sub 4-1

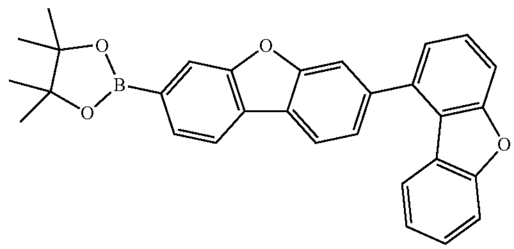

Sub 4-2

Under a nitrogen atmosphere, Sub 4-1 (15 g, 30 mmol) prepared in the above step and bis(pinacolato)diboron (15.3 g, 60 mmol) were added to 300 ml of 1,4-dioxane (Diox), which were stirred and refluxed. After that, potassium acetate (8.7 g, 90 mmol) was added and stirred sufficiently, and then bis(dibenzylideneacetone)palladium (0.5 g, 0.9 mmol) and tricyclohexylphosphine (0.5 g, 1.8 mmol) were added thereto. After the reaction for 6 hours, and after cooling to room temperature, the organic layer was filtered to remove a salt, and then the filtered organic layer was distilled. The distillate was again dissolved in 138 ml of chloroform, washed twice with water, and the organic layer was separated. After adding anhydrous magnesium sulfate and stirring, the filtrate was distilled under reduced pressure. The concentrated compound was recrystallized by chloroform and ethanol to prepare a white solid compound Sub 4-2 (10.6 g, 77%).

MS: $[M+H]^+$=461.2

Preparation Example F: Preparation of Intermediate Compound Sub 5-2

1) Preparation of Compound Sub 5-1

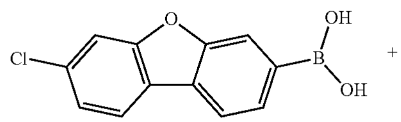

R-4

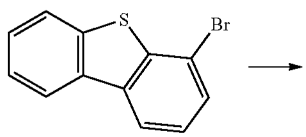

-continued

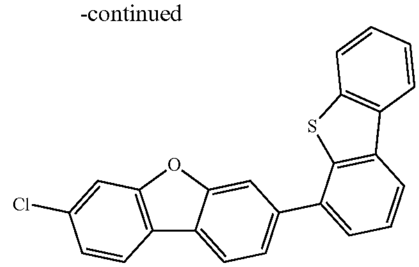

Sub 5-1

Under a nitrogen atmosphere, R-4 (20 g, 81.3 mmol) prepared in Preparation Example A and 4-bromodibenzo[b,d]thiophene (21.3 g, 81.3 mmol) were added to 400 ml of tetrahydrofuran, which were stirred and refluxed. After that, potassium carbonate (33.7 g, 243.9 mmol) was dissolved in 34 ml of water, and added, stirred thoroughly, and then tetrakis(triphenylphosphine)palladium(0) [$Pd(PPh_3)_4$] (2.8 g, 2.4 mmol) was added thereto. After the reaction for 1 hour, and after cooling to room temperature, the organic layer and the water layer were separated and the organic layer was distilled. The distillate was again dissolved in 624 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a yellow solid compound Sub 5-1 (20 g, 64%).

MS: $[M+H]^+$=385

2) Preparation of Compound Sub 5-2

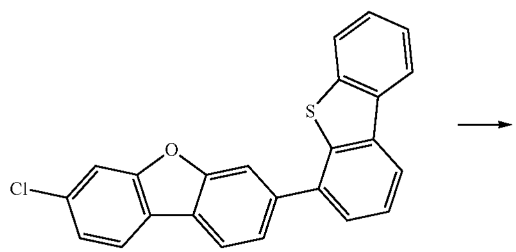

Sub 5-1

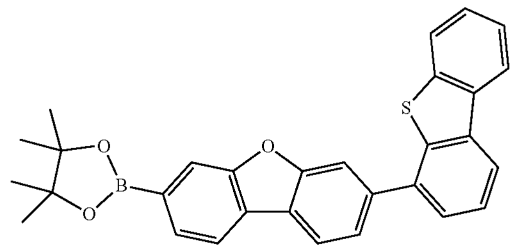

Sub 5-2

Under a nitrogen atmosphere, Sub 5-1 (15 g, 25 mmol) prepared in the above step and bis(pinacolato)diboron (12.7 g, 50 mmol) were added to 300 ml of 1,4-dioxane, which were stirred and refluxed. After that, potassium acetate (7.2 g, 75 mmol) was added and stirred sufficiently, and then bis(dibenzylideneacetone)palladium (0.4 g, 0.8 mmol) and tricyclohexylphosphine (0.4 g, 1.5 mmol) were added thereto. After the reaction for 5 hours, and after cooling to room temperature, the organic layer was filtered to remove a salt, and then the filtered organic layer was distilled. The distillate was again dissolved in 120 mL of chloroform, washed twice with water, and the organic layer was separated. After adding anhydrous magnesium sulfate and stirring, the filtrate was distilled under reduced pressure. The concentrated compound was recrystallized by chloroform and ethanol to prepare a white solid compound Sub 5-2 (8.4 g, 70%).

MS: $[M+H]^+$=479.2

Preparation Example 1: Preparation of Compound 1

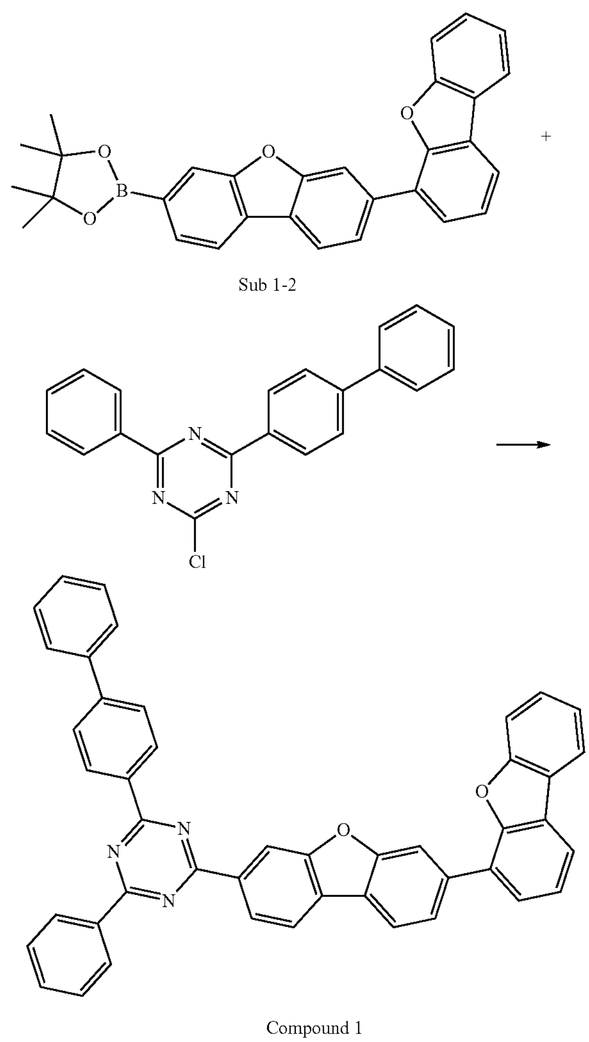

Sub 1-2

Compound 1

Under a nitrogen atmosphere, Sub 1-2 (10 g, 21.7 mmol) and 2-([1,1'-biphenyl]-4-yl)-4-chloro-6-phenyl-1,3,5-triazine (7.5 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) $[Pd(PPh_3)_4]$ (0.8 g, 0.7 mmol) was added thereto. After the reaction for 3 hours, and after cooling to room temperature, the organic layer and the water layer were separated and the organic layer was distilled. The distillate was again dissolved in 279 ml of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 1 (10.7 g, 77%).

MS: $[M+H]^+$=642.2

Preparation Example 2: Preparation of Compound 2

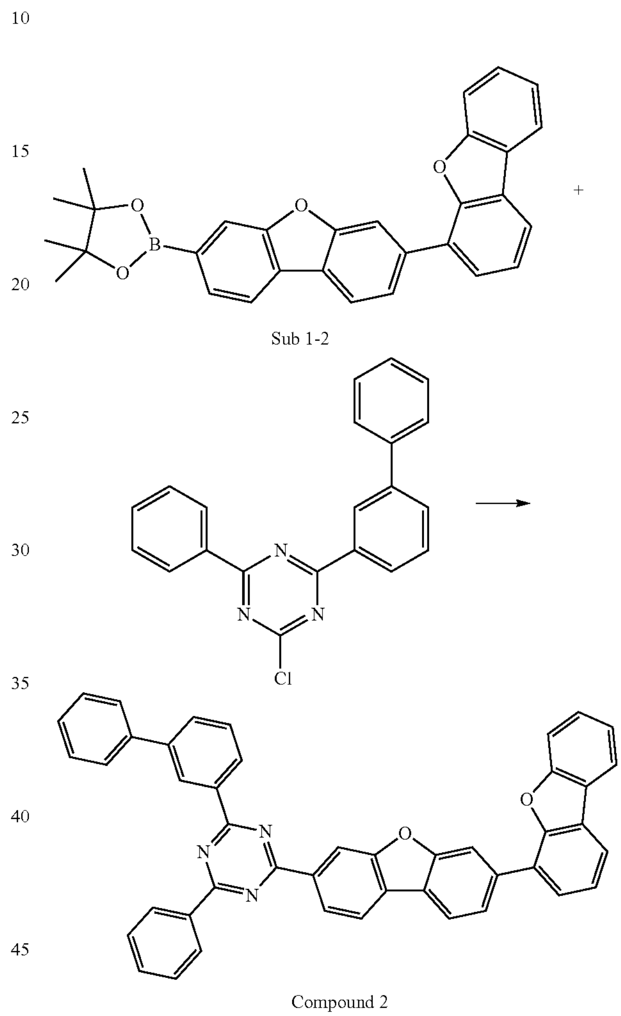

Sub 1-2

Compound 2

Under a nitrogen atmosphere, Sub 1-2 (10 g, 21.7 mmol) and 2-([1,1'-biphenyl]-3-yl)-4-chloro-6-phenyl-1,3,5-triazine (7.5 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) $[Pd(PPh_3)_4]$ (0.8 g, 0.7 mmol) was added thereto. After the reaction for 1 hour, and after cooling to room temperature, the organic layer and the water layer were separated and the organic layer was distilled. The distillate was again dissolved in 279 ml of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 2 (10.3 g, 74%).

MS: $[M+H]^+$=642.2

Preparation Example 3: Preparation of Compound 3

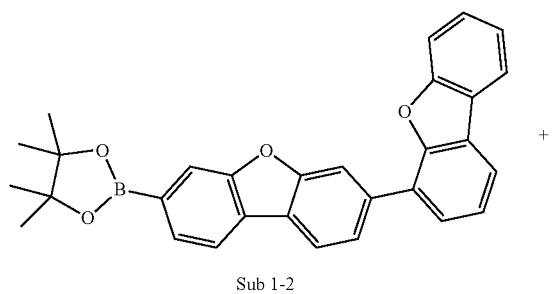

Sub 1-2

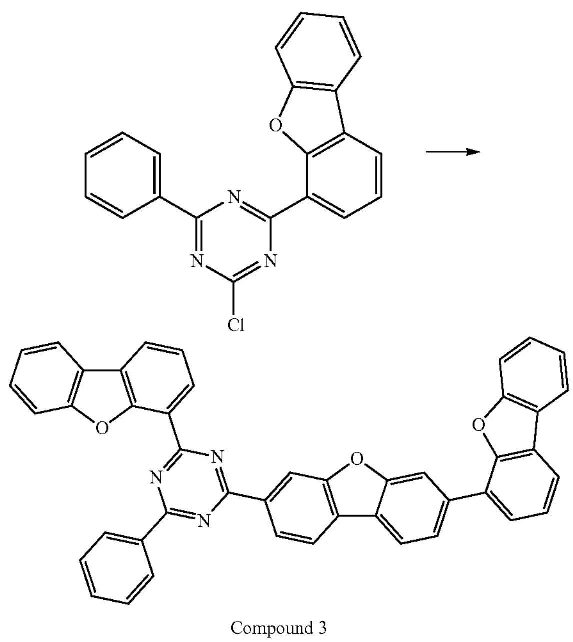

Compound 3

Under a nitrogen atmosphere, Sub 1-2 (10 g, 21.7 mmol) and 2-chloro-4-(dibenzo[b,d]furan-4-yl)-6-phenyl-1,3,5-triazine (7.8 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [Pd(PPh$_3$)$_4$] (0.8 g, 0.7 mmol) was added thereto. After the reaction for 3 hours, and after cooling to room temperature, the organic layer and the water layer were separated and the organic layer was distilled. The distillate was again dissolved in 285 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 3 (11.0 g, 77%).

MS: [M+H]$^+$=656.2

Preparation Example 4: Preparation of Compound 4

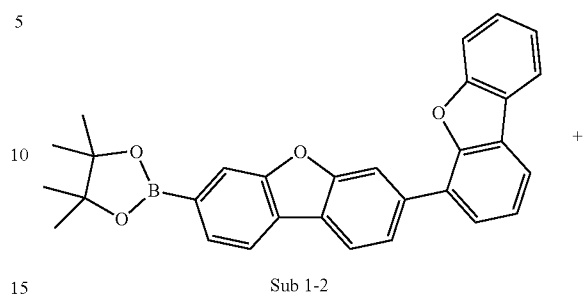

Sub 1-2

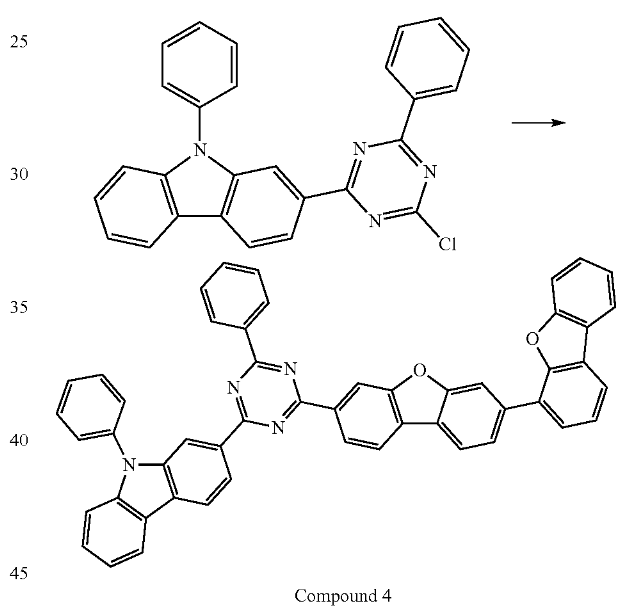

Compound 4

Under a nitrogen atmosphere, Sub 1-2 (10 g, 21.7 mmol) and 2-(4-chloro-6-phenyl-1,3,5-triazin-2-yl)-9-phenyl-9H-carbazole (9.4 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis (triphenylphosphine)palladium(0) [Pd(PPh$_3$)$_4$] (0.8 g, 0.7 mmol) was added thereto. After the reaction for 1 hour, and after cooling to room temperature, the organic layer and the water layer were separated and the organic layer was distilled. The distillate was again dissolved in 317 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 4 (12.1 g, 76%).

MS: [M+H]$^+$=731.2

Preparation Example 5: Preparation of Compound 5

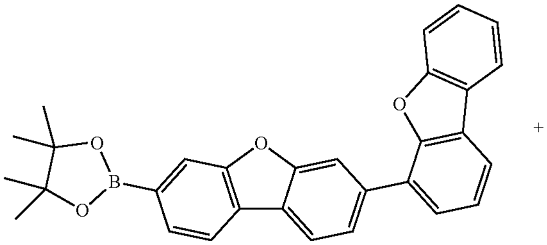

Sub 1-2

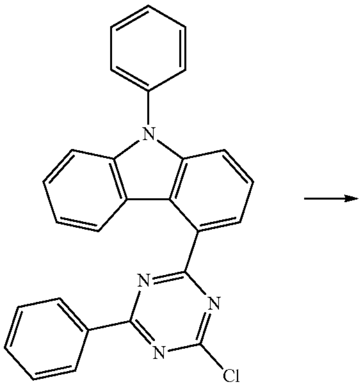

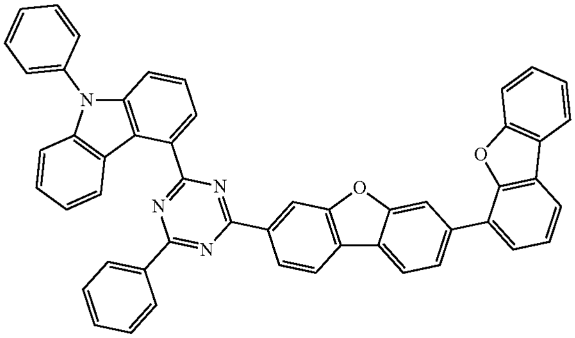

Compound 5

Under a nitrogen atmosphere, Sub 1-2 (10 g, 21.7 mmol) and 4-(4-chloro-6-phenyl-1,3,5-triazin-2-yl)-9-phenyl-9H-carbazole (9.4 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [$Pd(PPh_3)_4$] (0.8 g, 0.7 mmol) was added thereto. After the reaction for 3 hours, and after cooling to room temperature, the organic layer and the water layer were separated and the organic layer was distilled. The distillate was again dissolved in 317 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 5 (8.4 g, 53%).

MS: $[M+H]^+$=731.2

Preparation Example 6: Preparation of Compound 6

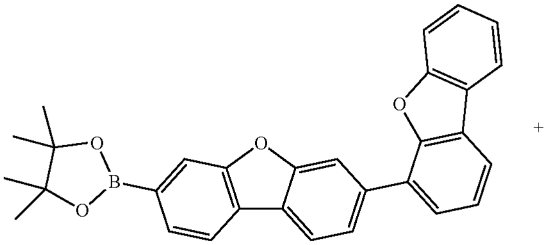

Sub 1-2

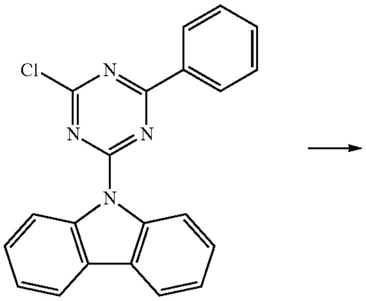

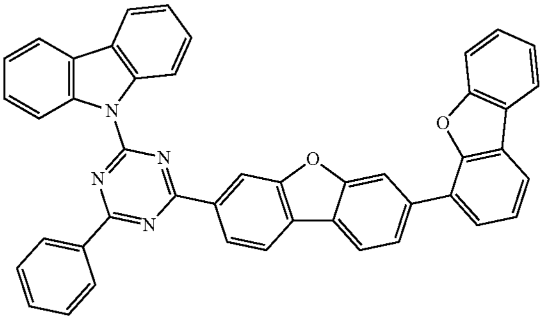

Compound 6

Under a nitrogen atmosphere, Sub 1-2 (10 g, 21.7 mmol) and 9-(4-chloro-6-phenyl-1,3,5-triazin-2-yl)-9H-carbazole (7.8 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [$Pd(PPh_3)_4$] (0.8 g, 0.7 mmol) was added thereto. After the reaction for 2 hours, and after cooling to room temperature, the organic layer and the water layer were separated and the organic layer was distilled. The distillate was again dissolved in 284 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 6 (9 g, 63%).

MS: $[M+H]^+$=655.2

Preparation Example 7: Preparation of Compound 7

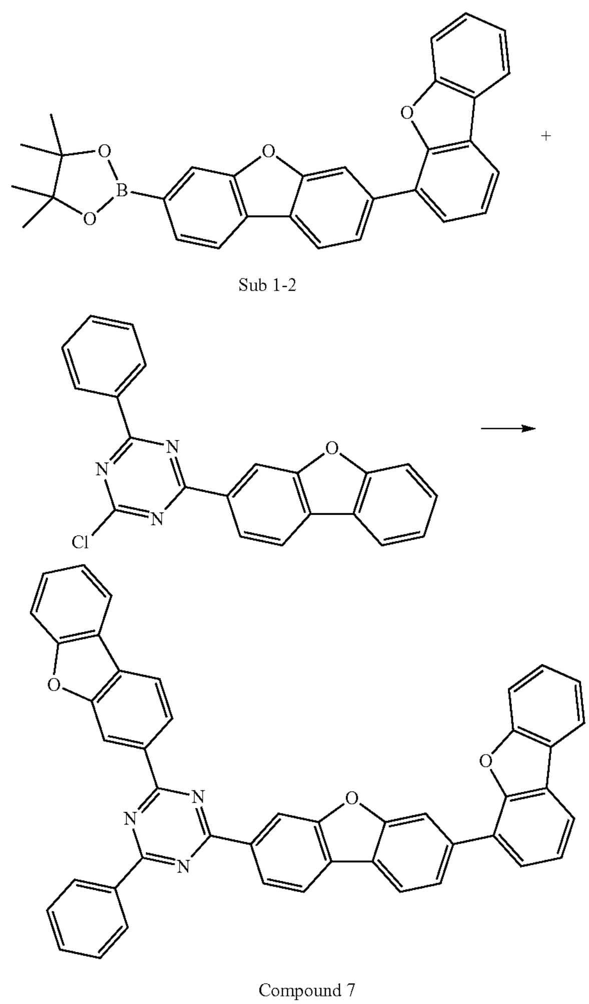

Sub 1-2

Compound 7

Under a nitrogen atmosphere, Sub 1-2 (10 g, 21.7 mmol) and 2-chloro-4-(dibenzo[b,d]furan-3-yl)-6-phenyl-1,3,5-triazine (7.8 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [$Pd(PPh_3)_4$] (0.8 g, 0.7 mmol) was added thereto. After the reaction for 1 hour, and after cooling to room temperature, the organic layer and the water layer were separated and the organic layer was distilled. The distillate was again dissolved in 285 ml of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 7 (11.1 g, 78%).

MS: [M H]=656.2

Preparation Example 8: Preparation of Compound 8

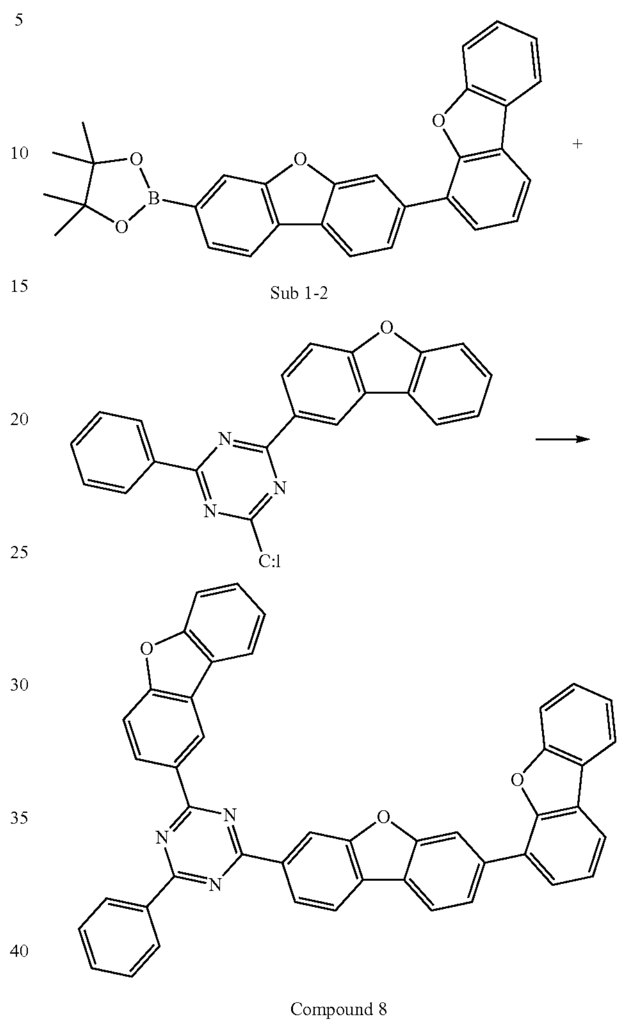

Sub 1-2

Compound 8

Under a nitrogen atmosphere, Sub 1-2 (10 g, 21.7 mmol) and 2-chloro-4-(dibenzo[b,d]furan-2-yl)-6-phenyl-1,3,5-triazine (7.8 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [$Pd(PPh_3)_4$] (0.8 g, 0.7 mmol) was added thereto. After the reaction for 1 hour, and after cooling to room temperature, the organic layer and the water layer were separated and the organic layer was distilled. The distillate was again dissolved in 285 ml of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 8 (7.3 g, 51%).

MS: $[M+H]^+$=656.2

Preparation Example 9: Preparation of Compound 9

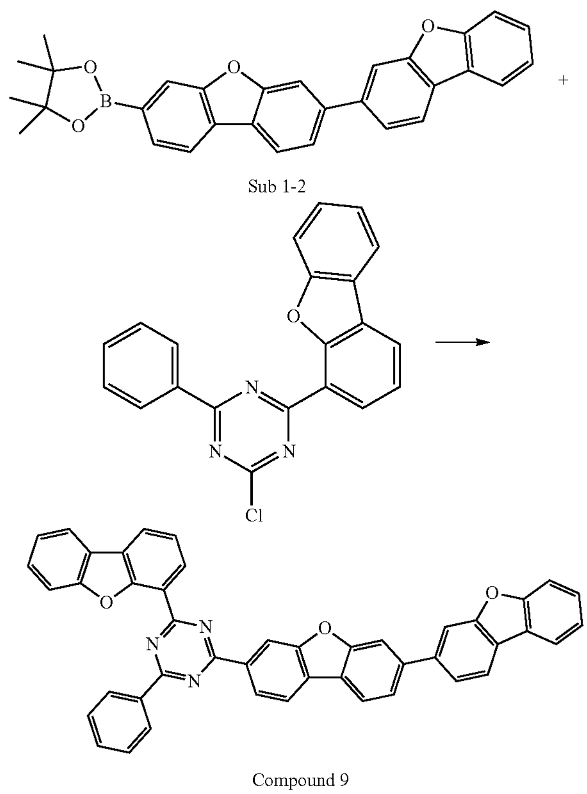

Sub 1-2

Compound 9

Under a nitrogen atmosphere, Sub 2-2 (10 g, 21.7 mmol) and 2-chloro-4-(dibenzo[b,d]furan-4-yl-6-phenyl-1,3,5-triazine (7.8 g, 21.7 mol) were added to 200 L of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [$Pd(PPh_3)_4$] (0.8 g, 0.7 mmol) was added thereto. After the reaction for 1 hour, and after cooling to room temperature, the organic layer and the water layer were separated and the organic layer was distilled. The distillate was again dissolved in 285 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 9 (9.1 g, 64%).

MS: $[M+H]^+$=656.2

Preparation Example 10: Preparation of Compound 10

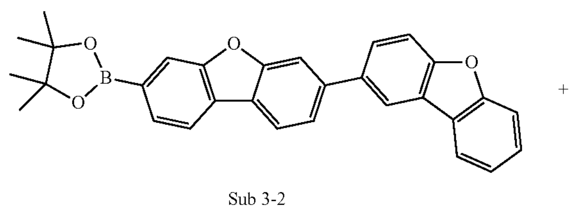

Sub 3-2

-continued

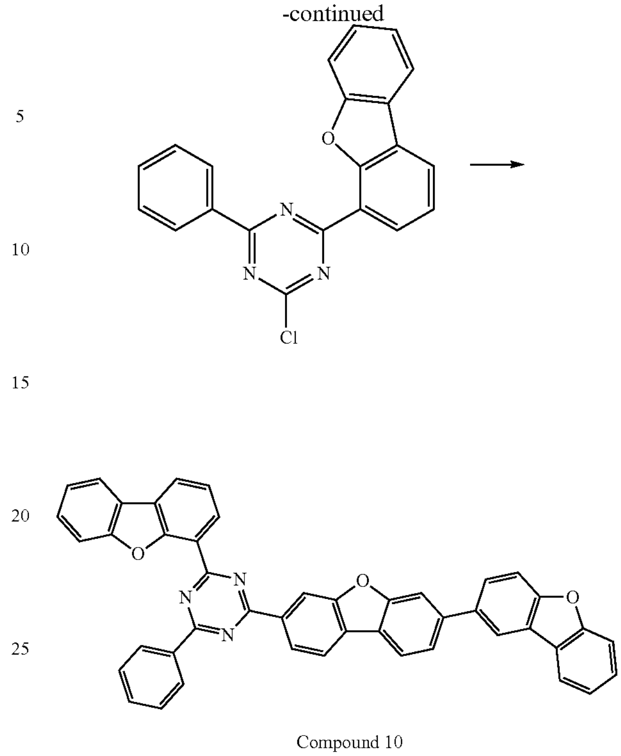

Compound 10

Under a nitrogen atmosphere, Sub 3-2 (10 g, 21.7 mmol) and 2-chloro-4-(dibenzo[b,d]furan-4-yl)-6-phenyl-1,3,5-triazine (7.8 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [$Pd(PPh_3)_4$] (0.8 g, 0.7 mmol) was added thereto. After the reaction for 2 hours, and after cooling to room temperature, the organic layer and the water layer were separated and the organic layer was distilled. The distillate was again dissolved in 285 mL of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 10 (8.5 g, 60%).

MS: $[M+H]^+$=656.2

Preparation Example 11: Preparation of Compound 11

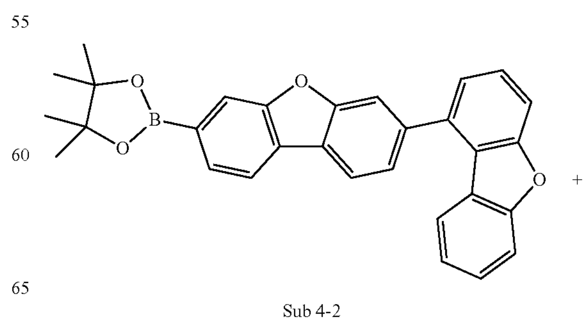

Sub 4-2

-continued

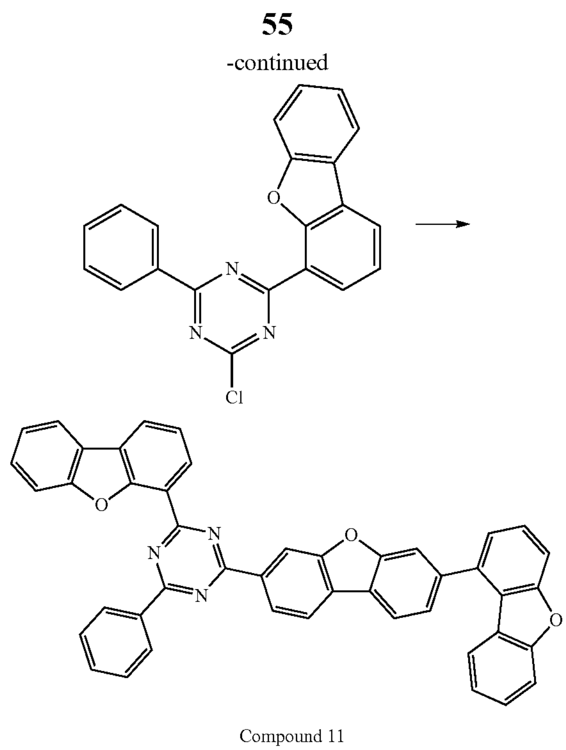

Compound 11

Under a nitrogen atmosphere, Sub 4-2 (10 g, 21.7 mmol) and 2-chloro-4-(dibenzo[b,d]furan-4-yl)-6-phenyl-1,3,5-triazine (7.8 g, 21.7 mmol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [$Pd(PPh_3)_4$] (0.8 g, 0.7 mmol) was added thereto. After the reaction for 3 hours, and after cooling to room temperature, the organic layer and the water layer were separated and the organic layer was distilled. The distillate was again dissolved in 285 ml of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 11 (7.8 g, 55%).

MS: $[M+H]^+$=656.2

Preparation Example 12: Preparation of Compound 12

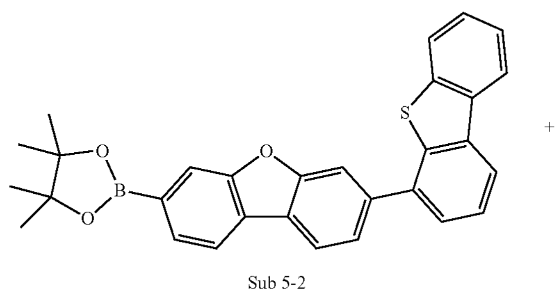

Sub 5-2

-continued

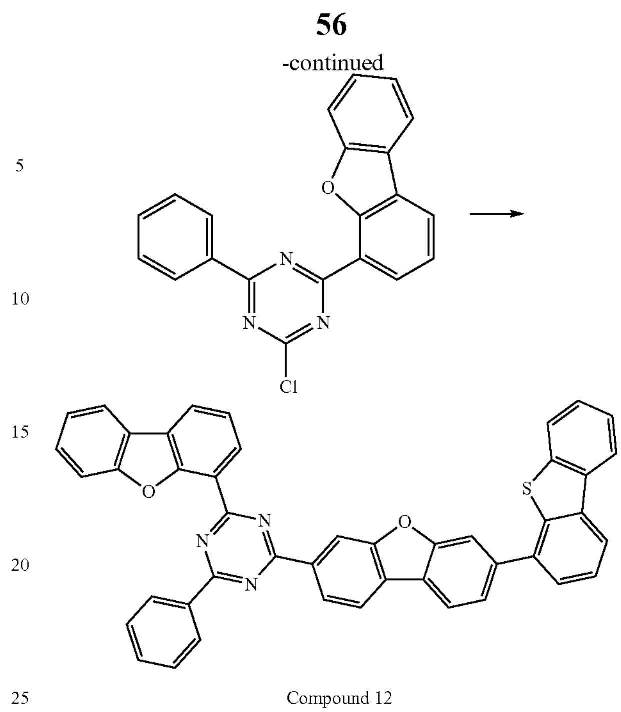

Compound 12

Under a nitrogen atmosphere, Sub 5-2 (10 g, 21.7 mmol) and 2-chloro-4-(dibenzo[b,d]furan-4-yl)-6-phenyl-1,3,5-triazine (7.8 g, 21.7 mol) were added to 200 ml of tetrahydrofuran, which were stirred and refluxed. After that, potassium carbonate (9 g, 65.2 mmol) was dissolved in 9 ml of water and added, stirred thoroughly, and then tetrakis(triphenylphosphine)palladium(0) [$Pd(PPh_3)_4$] (0.8 g, 0.7 mmol) was added thereto. After the reaction for 3 hours, and after cooling to room temperature, the organic layer and the water layer were separated and the organic layer was distilled. The distillate was again dissolved in 292 ml of chloroform, washed twice with water, and the organic layer was separated. After adding anhydrous magnesium sulfate and stirring, the filtrate was distilled under reduced pressure. The concentrated compound was recrystallized by chloroform and ethyl acetate to prepare a white solid compound 12 (10.8 g, 74%).

MS: $[M+H]^+$=672.2

Example 1

A glass substrate on which ITO (indium tin oxide) was coated as a thin film to a thickness of 1300 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. In addition, the substrate was cleaned for 5 minutes using oxygen plasma, and then transferred to a vacuum depositor.

On the ITO transparent electrode thus prepared, the following compound HI-1 was thermally vacuum deposited to a thickness of 50 Å to form a hole injection layer. The following compound HT-1 was thermally vacuum deposited on the hole injection layer to a thickness of 250 Å to form a hole transport layer, and the following compound HT-2 was vacuum deposited on the hole transport layer to a thickness of 50 Å to form an electron blocking layer.

The compound 1 prepared in the previous Preparation Example 1, the following compound YGH-1, and a phosphorescent dopant YGD-1 were co-deposited at a weight ratio of 44:44:12 on the electron blocking layer to form a light emitting layer with a thickness of 400 Å.

The following compound ET-1 was vacuum deposited on the light emitting layer to a thickness of 250 Å to form an electron transport layer, and the following compound ET-2 and Li were vacuum deposited at a weight ratio of 98:2 to form an electron injection layer with a thickness of 100 Å. Aluminum was deposited on the electron injection layer to a thickness of 1000 Å to form a cathode.

HI-1

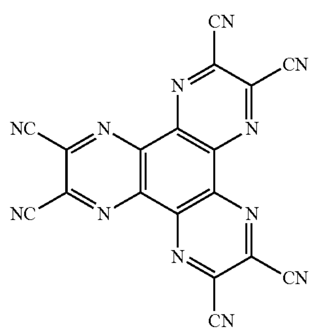

HT-1

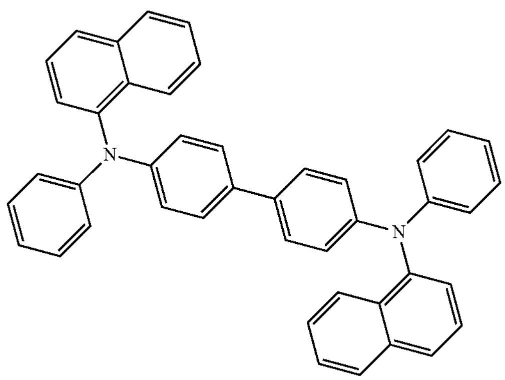

-continued

HT-2

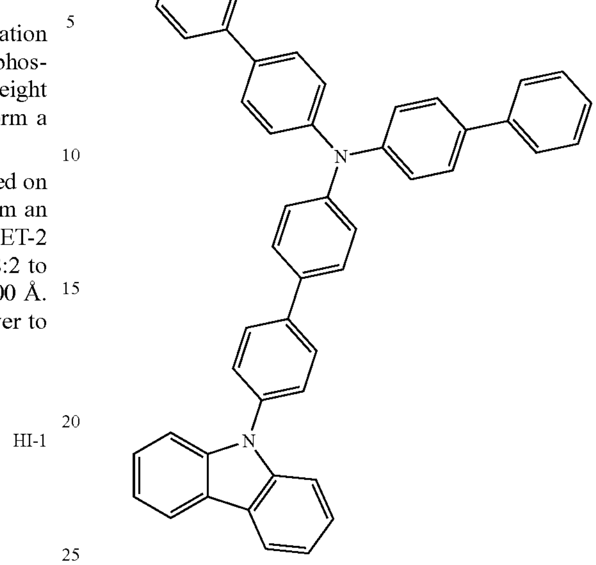

YGH-1

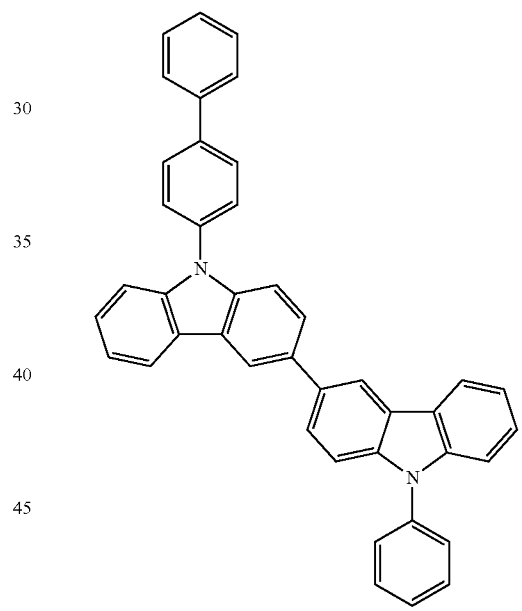

YGD-1

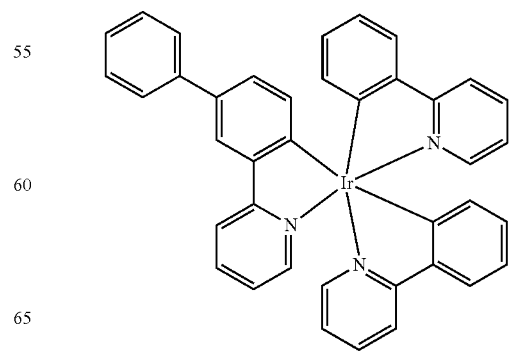

-continued

ET-1

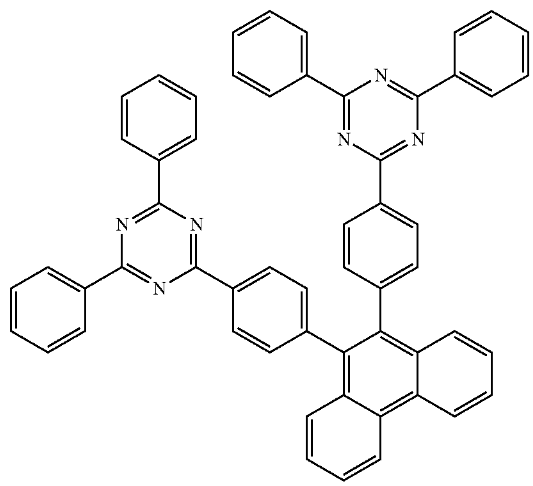

ET-2

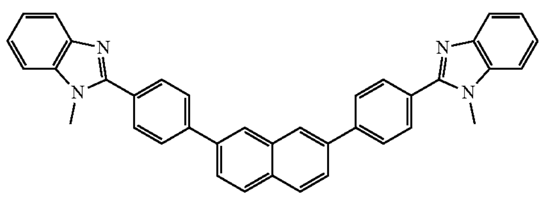

In the above-mentioned process, the vapor deposition rate of the organic material was maintained at 0.4 to 0.7 Å/s, the deposition rates of aluminum were maintained at 2 Å/s and, and the degree of vacuum during the deposition was maintained at 1×10−7 to 5×10−8 Torr.

Examples 2 to 12

An organic light emitting device was manufactured in the same manner as in Example 1, except that the compounds shown in Table 1 below were used instead of Compound 1 of Preparation Example 1 in Example 1.

The structures of the compounds used in the Examples 1 to 12 are as follows:

Compound 1

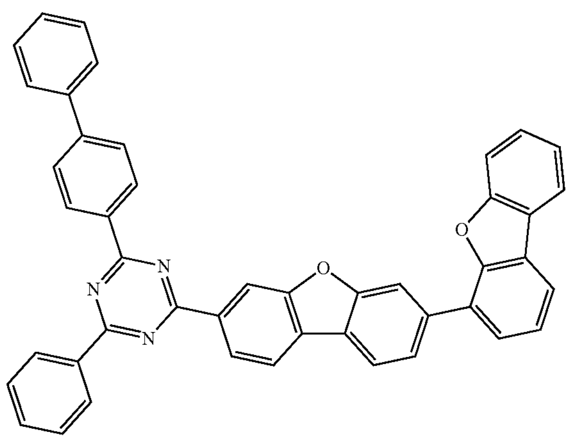

-continued

Compound 2

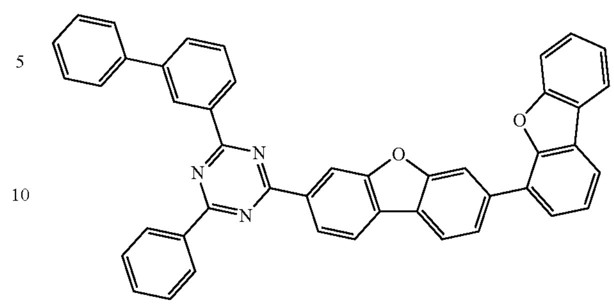

Compound 3

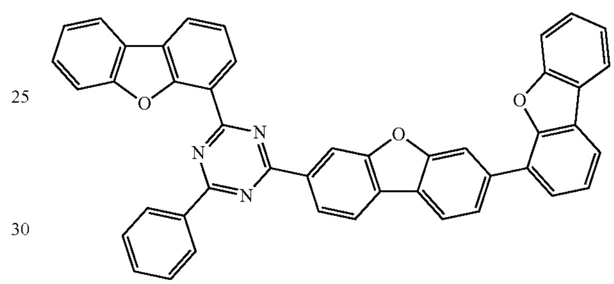

Compound 4

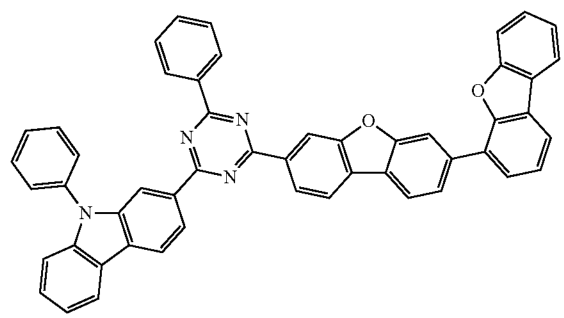

Compound 5

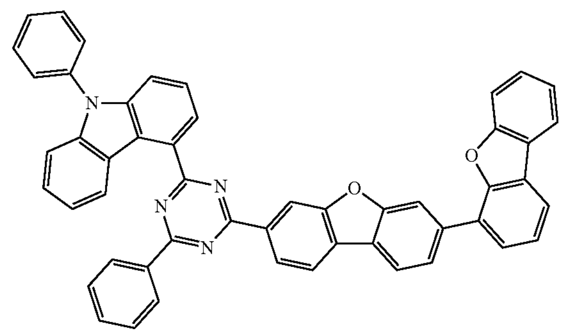

-continued

Compound 6

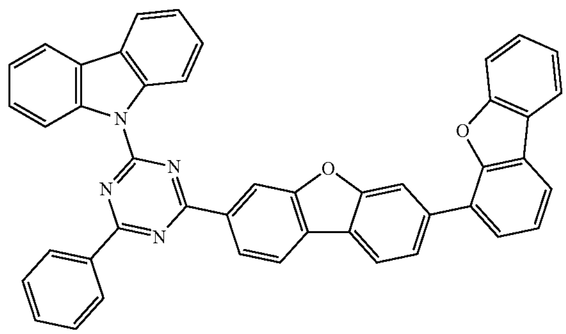

Compound 7

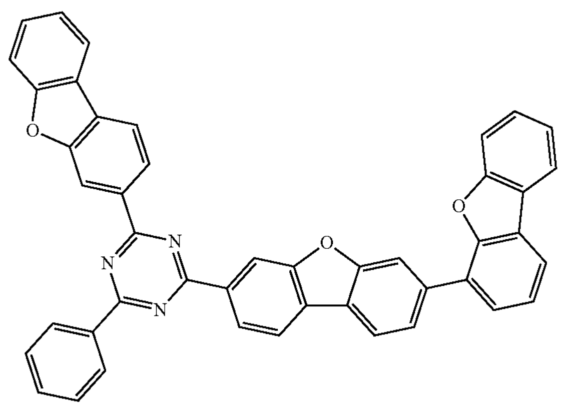

Compound 8

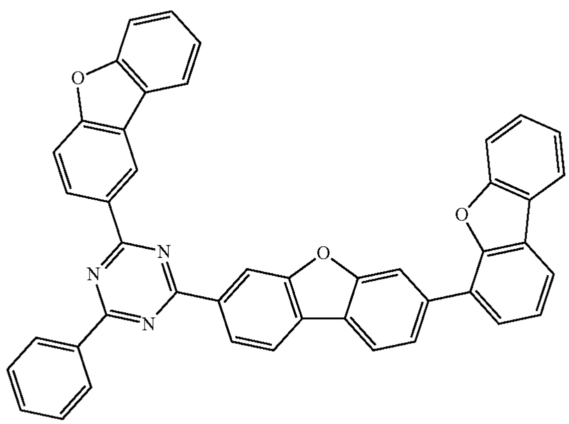

Compound 9

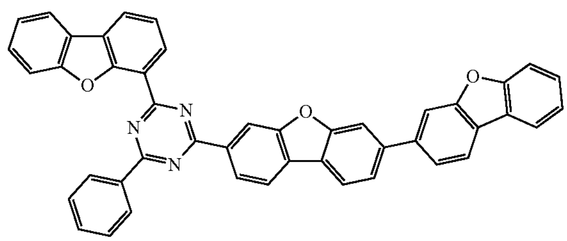

-continued

Compound 10

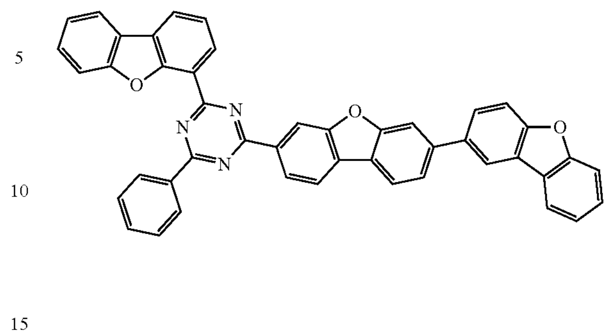

Compound 11

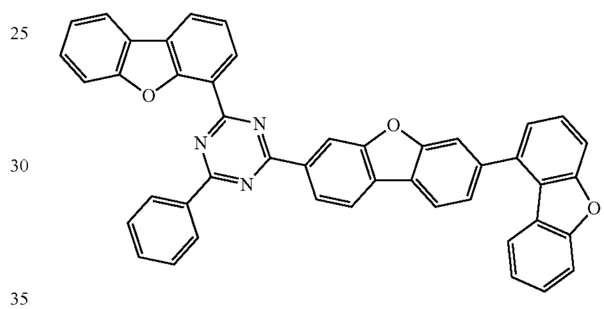

Compound 12

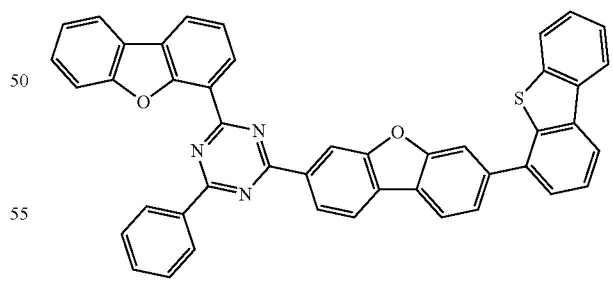

Comparative Examples 1 to 4

An organic light emitting device was manufactured in the same manner as in Example 1, except that the compounds shown in Table 1 below were used instead of Compound 1 of Preparation Example 1 in Example 1. The structures of the compounds CE1 to CE4 in Table 1 below are as follows.

CE1
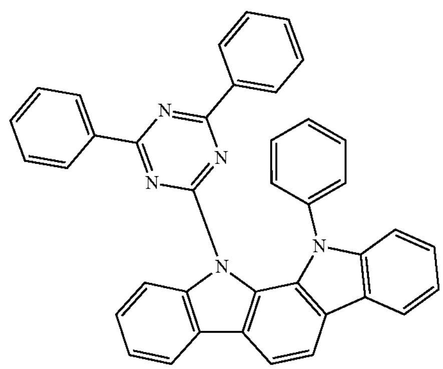
CE2
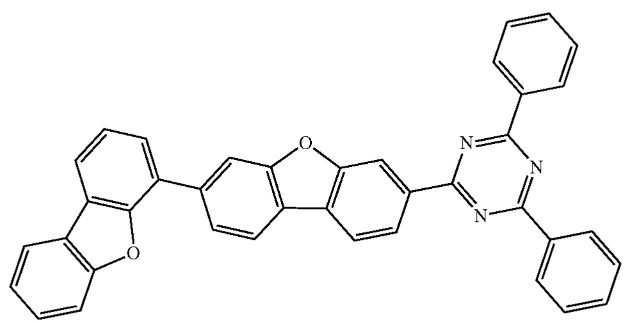
CE3
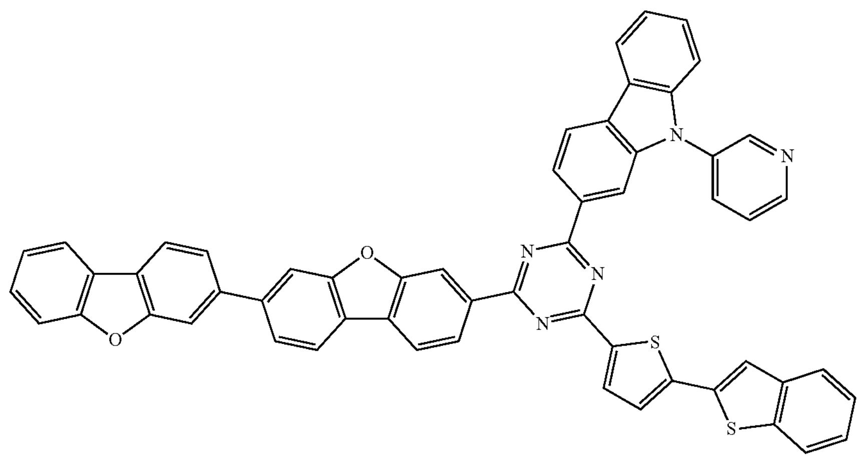
CE4
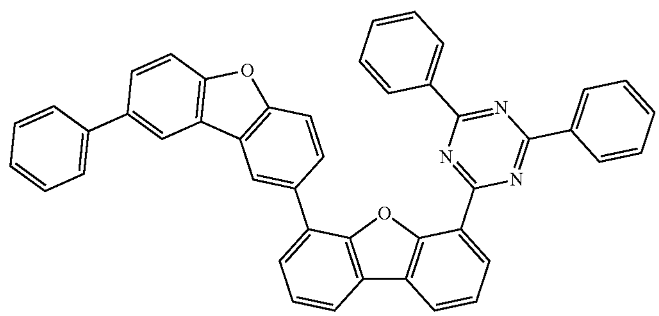

Experimental Example 1

The voltage, the efficiency, the color coordinates, and the lifetime were measured by applying a current to the organic light emitting devices manufactured in the Examples 1 to 12 and Comparative Examples 1 to 4 above, and the results are shown in Table 1 below. At this time, the lifetime ($LT_{95}$) means the time required for the luminance to be reduced to 95% of the initial luminance.

TABLE 1

| | Compound (host) | Voltage (V) (@10 $mA/cm^2$) | Efficiency (Cd/A) (@10 $mA/cm^2$) | Color coordinates (x, y) | Lifetime (h) ($LT_{95}$ at 50 $mA/cm^2$) |
|---|---|---|---|---|---|
| Example 1 | Compound 1 | 4.1 | 83 | 0.46, 0.54 | 191 |
| Example 2 | Compound 2 | 4.2 | 85 | 0.46, 0.54 | 215 |
| Example 3 | Compound 3 | 4.1 | 84 | 0.46, 0.54 | 194 |
| Example 4 | Compound 4 | 4.3 | 82 | 0.46, 0.54 | 177 |
| Example 5 | Compound 5 | 4.2 | 83 | 0.46, 0.53 | 165 |
| Example 6 | Compound 6 | 4.4 | 81 | 0.46, 0.54 | 211 |
| Example 7 | Compound 7 | 4.2 | 83 | 0.46, 0.54 | 230 |
| Example 8 | Compound 8 | 4.3 | 83 | 0.46, 0.54 | 177 |
| Example 9 | Compound 9 | 4.2 | 83 | 0.46, 0.54 | 165 |
| Example 10 | Compound 10 | 4.2 | 81 | 0.46, 0.54 | 184 |
| Example 11 | Compound 11 | 3.9 | 80 | 0.46, 0.53 | 161 |
| Example 12 | Compound 12 | 4.2 | 81 | 0.46, 0.53 | 222 |
| Comparative Example 1 | CE1 | 4.0 | 79 | 0.46, 0.54 | 98 |
| Comparative Example 2 | CE2 | 4.2 | 77 | 0.46, 0.55 | 130 |
| Comparative Example 3 | CE3 | 6.1 | 46 | 0.51, 0.50 | 14 |
| Comparative Example 4 | CE4 | 4.3 | 74 | 0.47, 0.55 | 77 |

As shown in Table 1, it was confirmed that the organic light emitting device using the compound of the present disclosure as a host material in the light emitting layer exhibited excellent properties in terms of efficiency and stability of the organic light emitting device.

Specifically, it can be seen that the organic light emitting device of the examples employing the compound represented by Chemical Formula 1 exhibited an equivalent level or lower of voltage, high efficiency, and significantly improved lifetime characteristics, as compared with an organic light emitting device of Comparative Example 2 employing a CE2 compound having only a phenyl group as a substituent of a triazinyl group, Comparative Example 3 employing a CE3 compound having a substituent not included in Formula 1 as a substituent of a triazinyl group, and Comparative Example 4 employing a CE4 compound having a triazinyl group bonded to a different position from that of the compound represented by Chemical Formula 1

| Description of Reference Numerals | |
|---|---|
| 1: substrate | 2: anode |
| 3: light emitting layer | 4: cathode |
| 5: hole injection layer | 6: hole transport layer |
| 7: electron blocking layer | 8: electron transport layer |
| 9: electron injection layer | |

What is claimed is:

1. A compound represented by the following Chemical Formula 1:

[Chemical Formula 1]

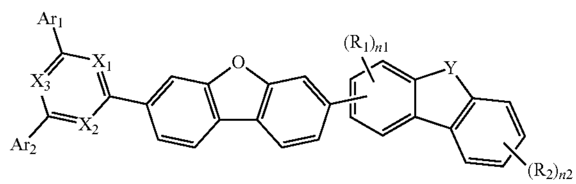

wherein, in Chemical Formula 1, $X_1$ to $X_3$ are each independently N or CH, and at least two of $X_1$ to $X_3$ are N, Y is O or S, $Ar_1$ is phenyl, biphenylyl, naphthyl, phenanthrenyl, or dimethylfluorenyl, $Ar_2$ is carbazolyl, carbazolylphenyl, dibenzofuranyl, or dibenzothiophenyl, wherein $Ar_1$ and $Ar_2$ are each independently unsubstituted or substituted with one or more substituents each independently selected from the group consisting of a $C_{1-20}$ alkyl, and a $C_{6-20}$ aryl, $R_1$ and $R_2$ are each independently a substituted or unsubstituted $C_{6-60}$ aryl; or a substituted or unsubstituted $C_{2-60}$ heteroaryl containing one or more heteroatoms selected from the group consisting of N, O, and S, n1 is an integer of 0 to 3, and n2 is an integer of 0 to 4.

2. The compound according to claim 1, wherein $X_1$ to $X_3$ are N.

3. The compound according to claim 1, wherein $Ar_1$ is one selected from the group consisting of the following:

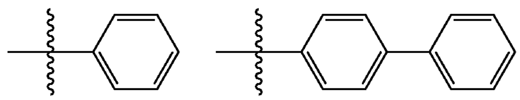

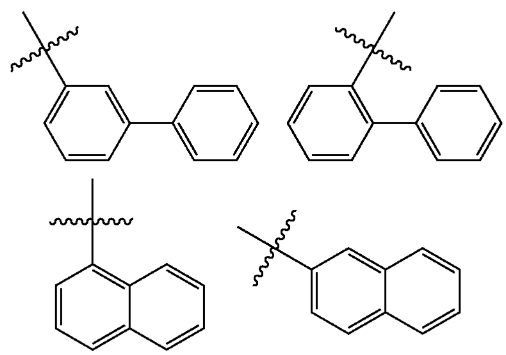

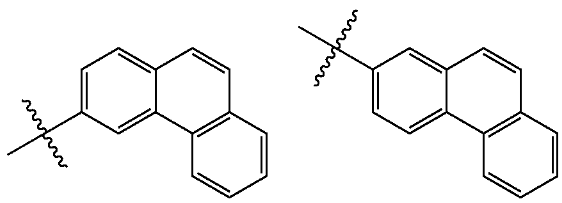

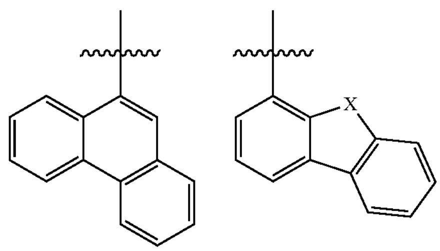

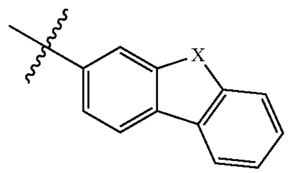

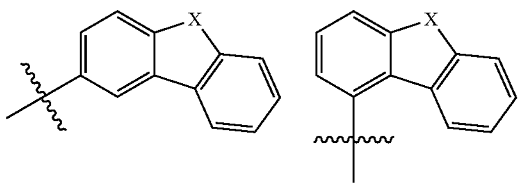

wherein X is C(methyl)$_2$, and wherein $Ar_2$ is one selected from the group consisting of the following:

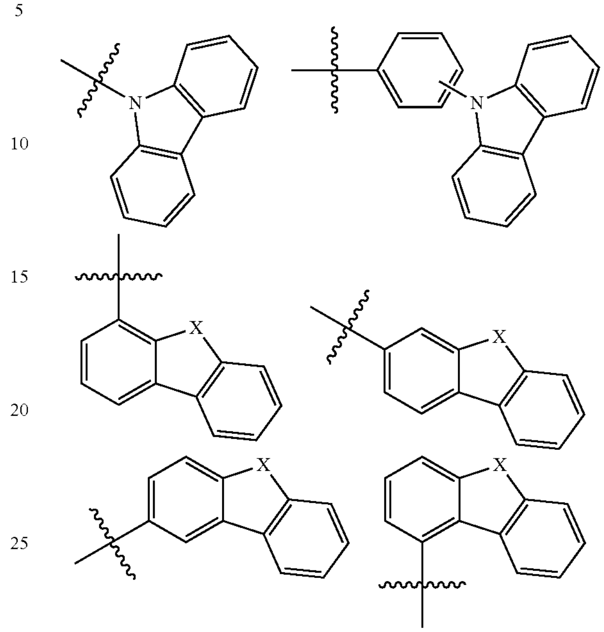

wherein X is O, S, or N(phenyl).

4. The compound according to claim 1, wherein $R_1$ and $R_2$ are phenyl.

5. The compound according to claim 1, wherein n1 is 0 or 1, and n2 is 0, 1, or 2.

6. The compound according to claim 1, wherein the compound is represented by any one of the following Chemical Formulae 1-1 to 1-5:

[Chemical Formula 1-1]

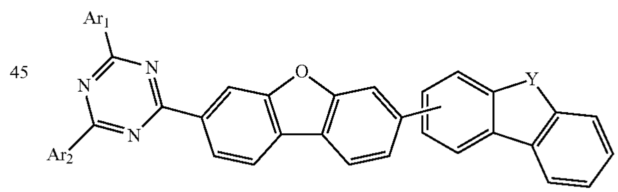

[Chemical Formula 1-2]

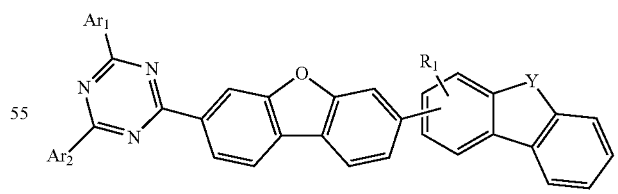

[Chemical Formula 1-3]

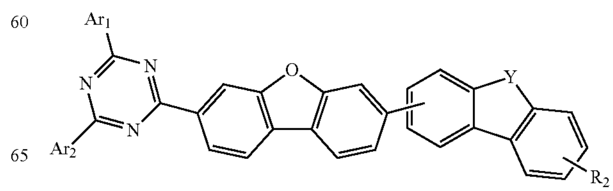

-continued
[Chemical Formula 1-4]
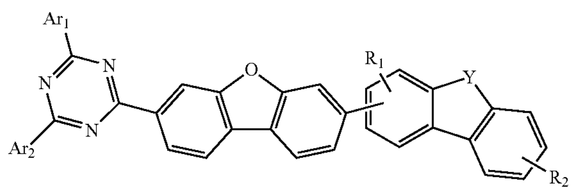
[Chemical Formula 1-5]
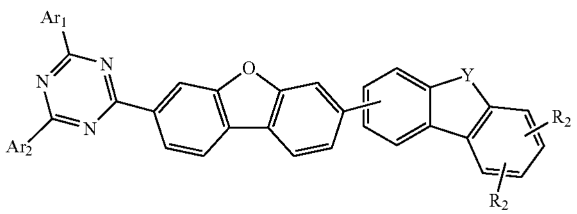
wherein, in Chemical Formulae 1-1 to 1-5,
Y, $Ar_1$, $Ar_2$, $R_1$, and $R_2$ are the same as defined in claim 1.
7. The compound according to claim 1,
wherein the compound is any one selected from the group consisting of the following compounds:
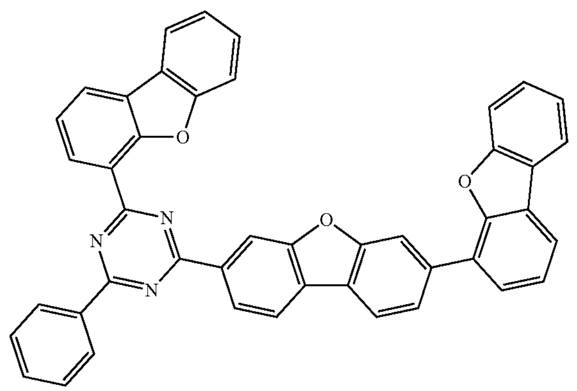
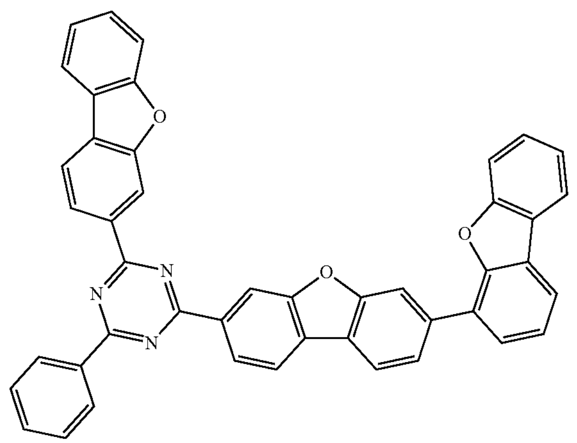
-continued
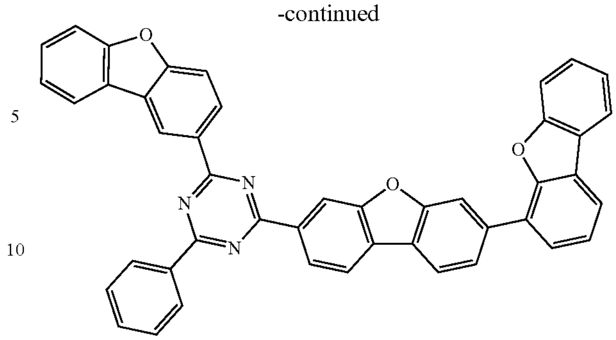
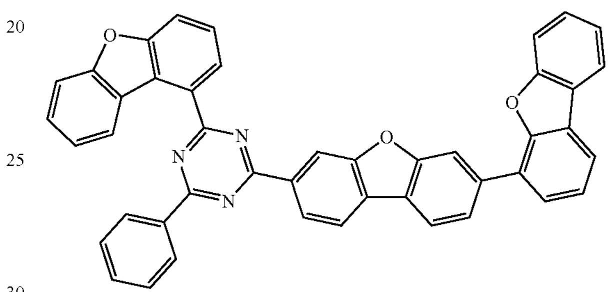
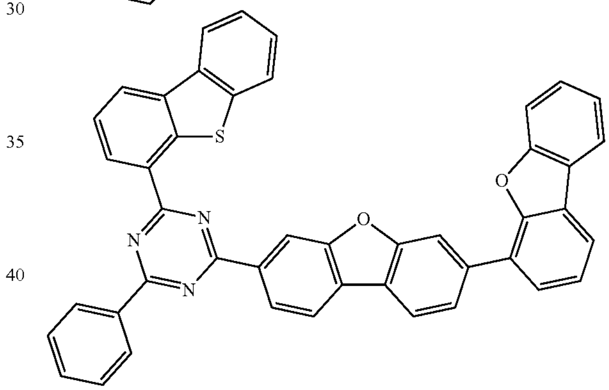
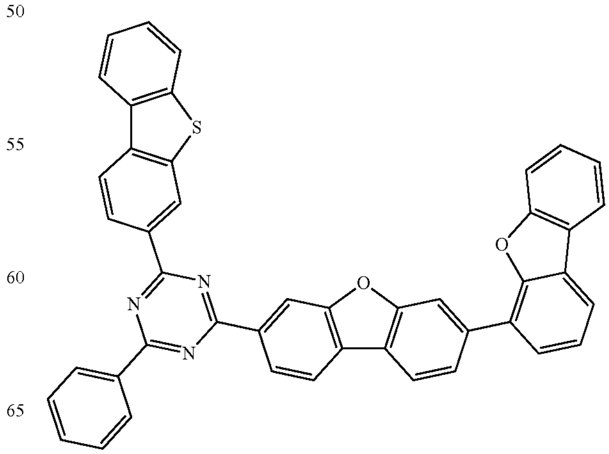

-continued
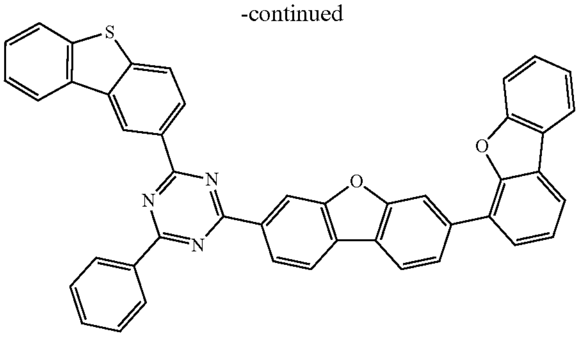
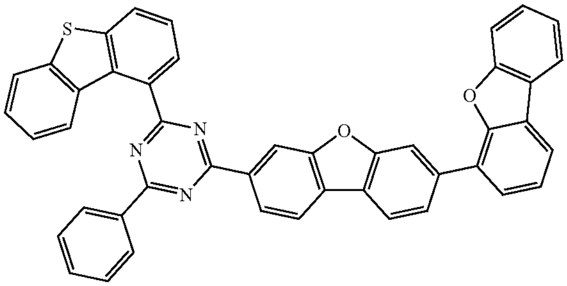
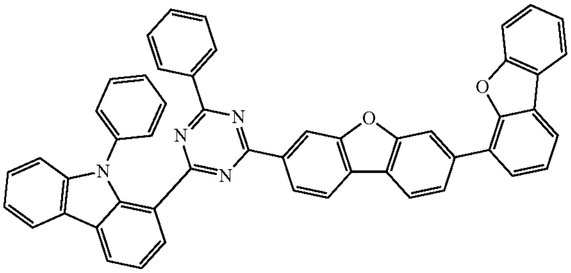
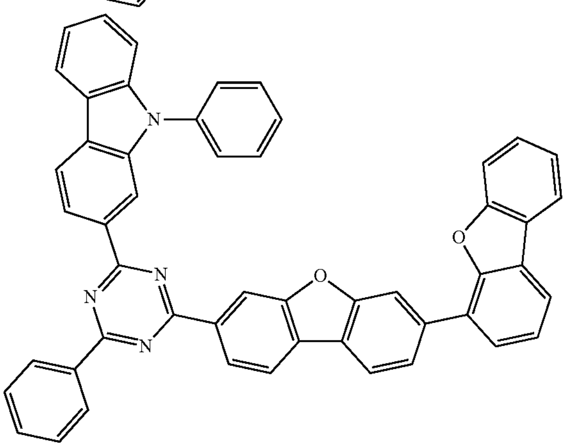
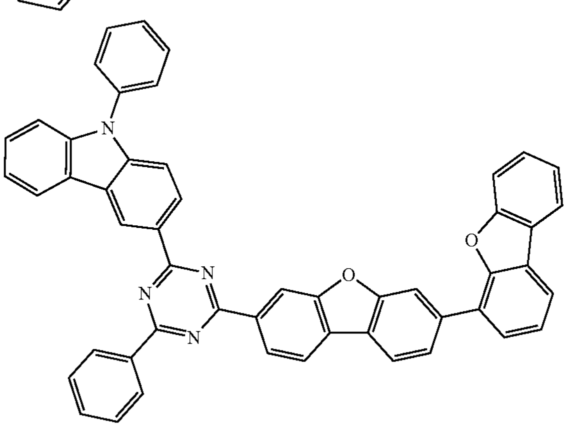
-continued
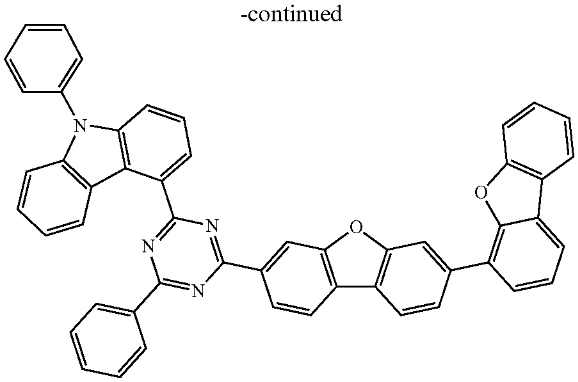
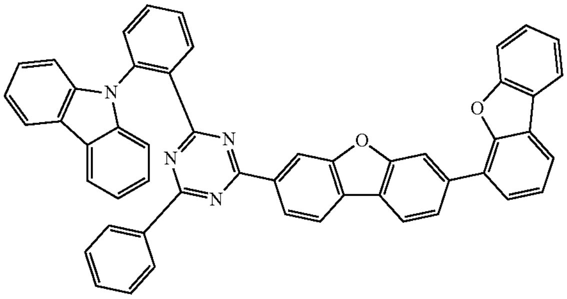
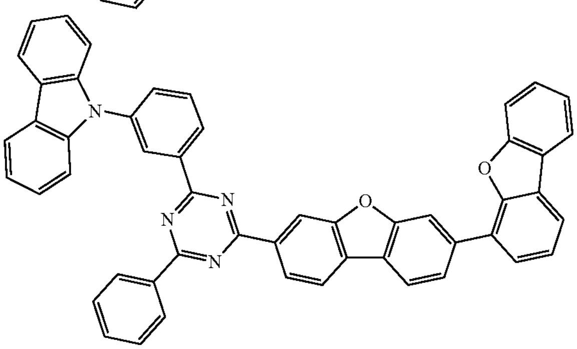
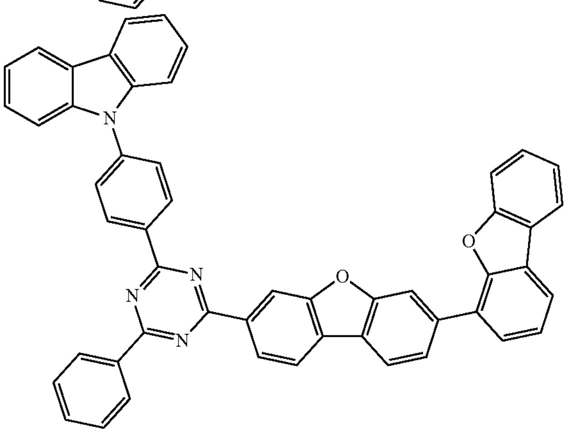
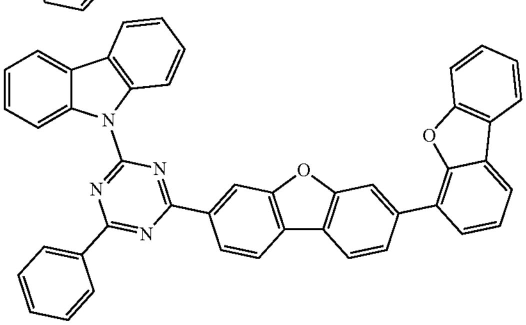

-continued
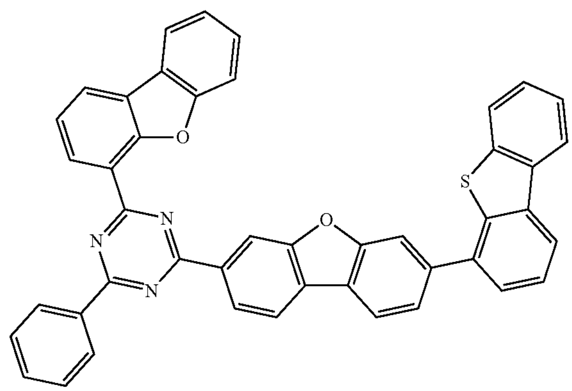
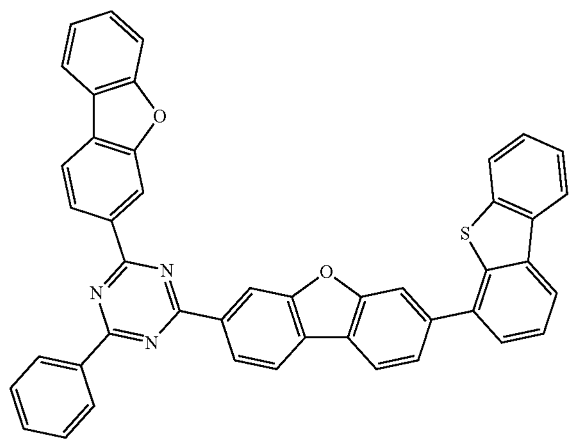
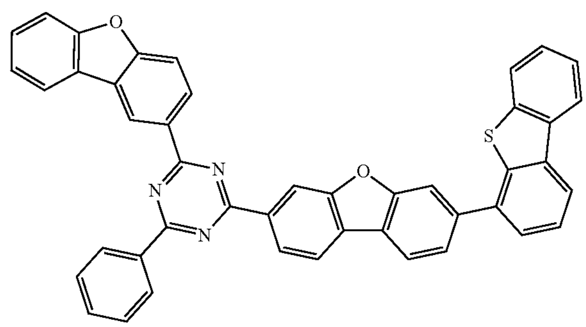
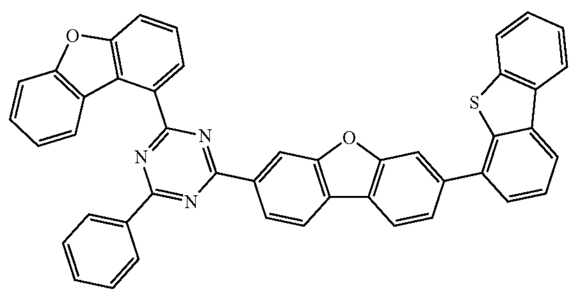
-continued
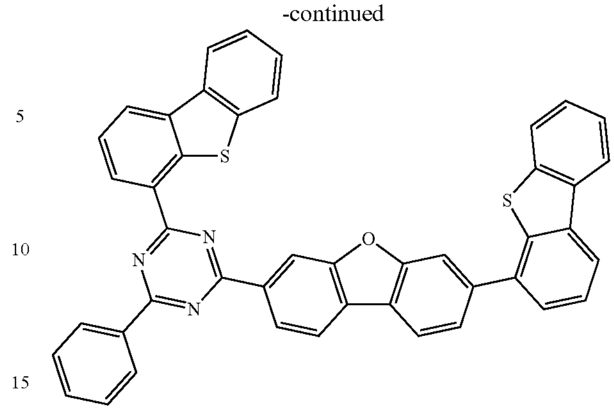
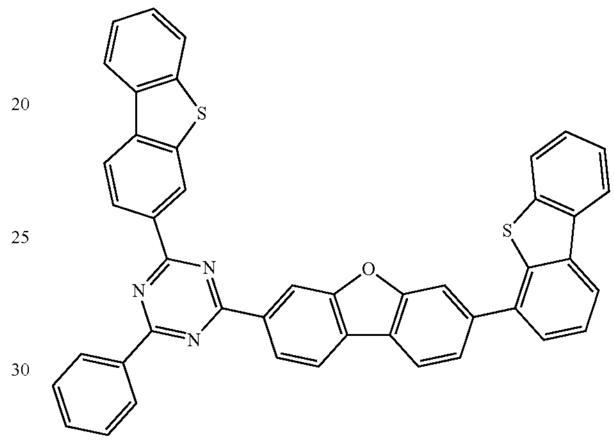
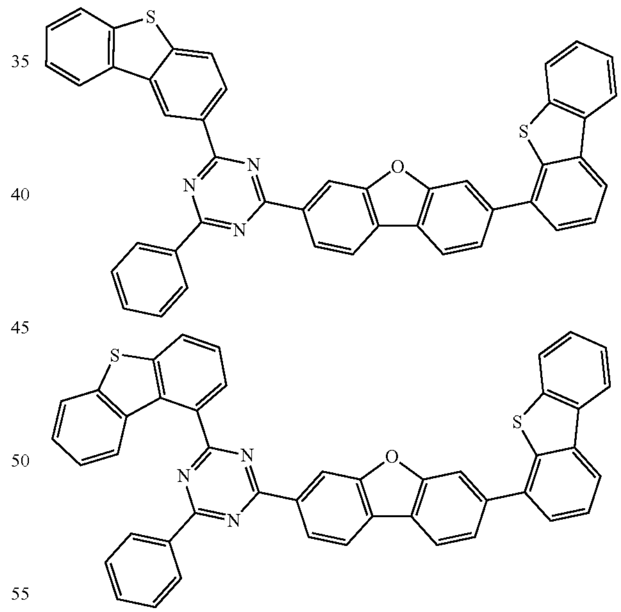
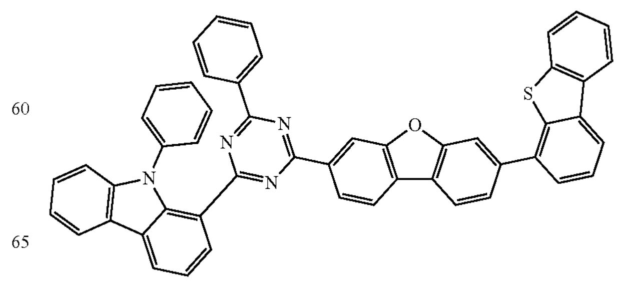

-continued
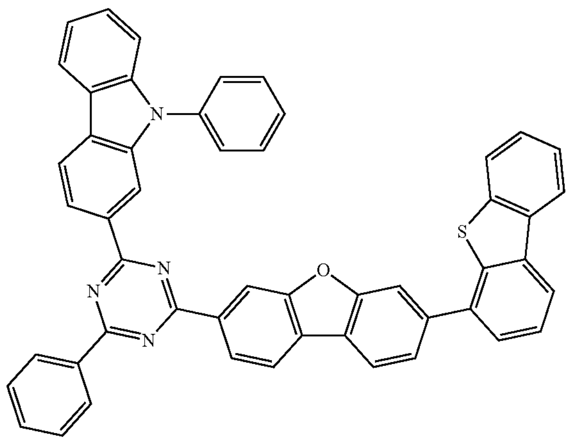
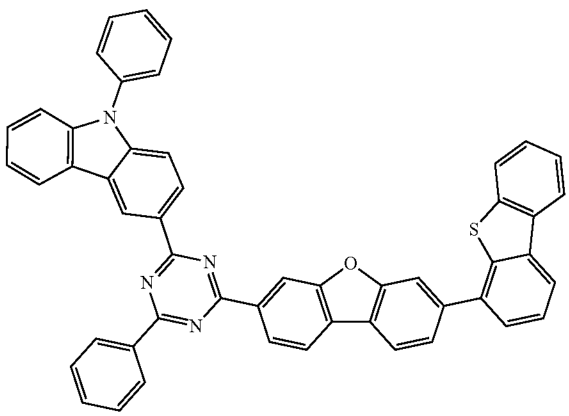
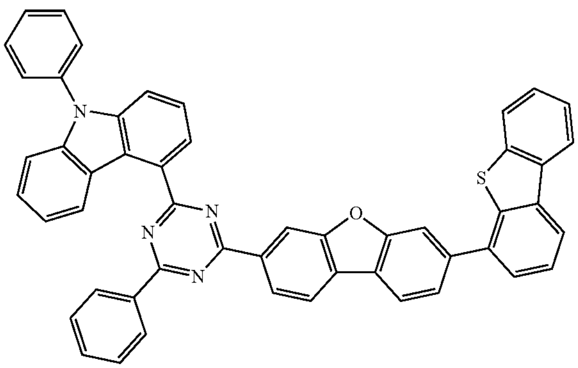
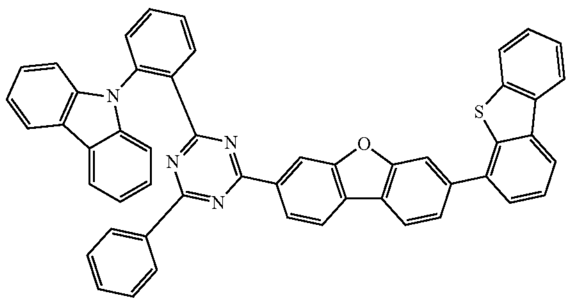
-continued
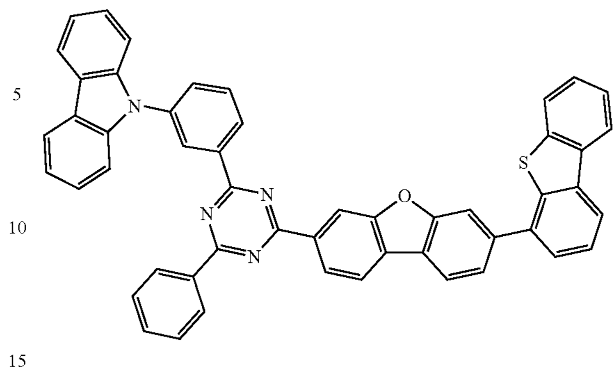
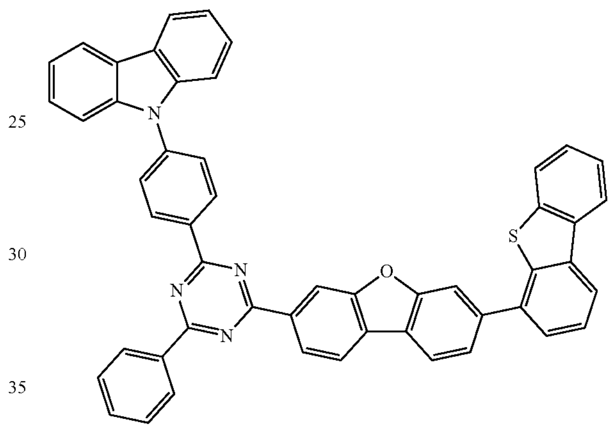
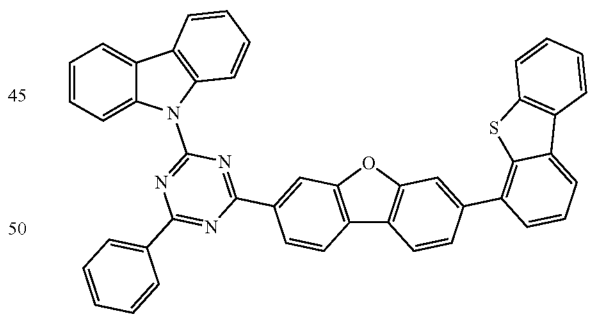
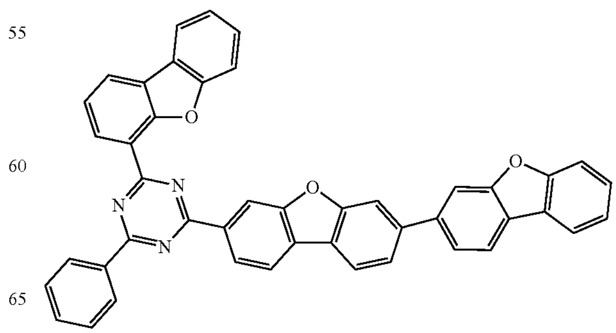

-continued
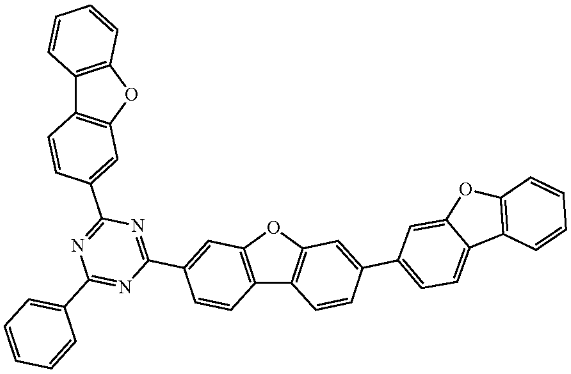
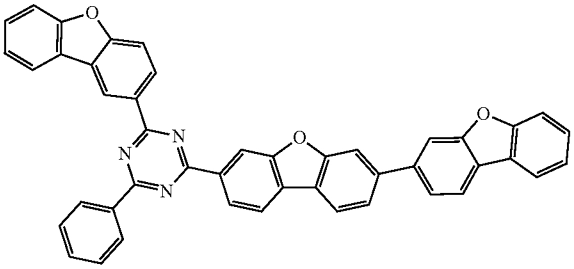
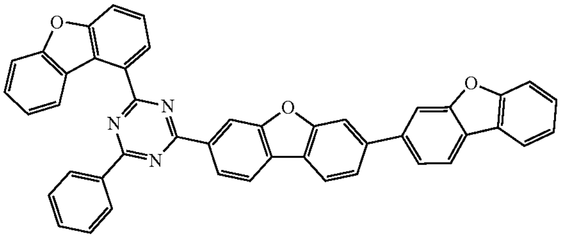
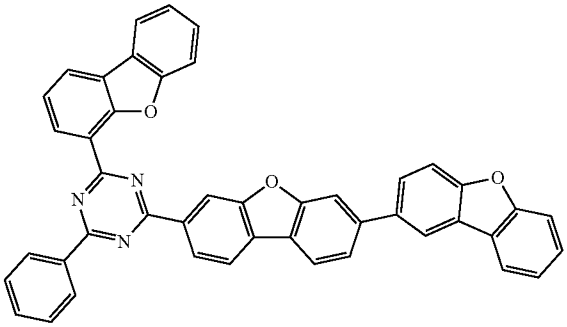
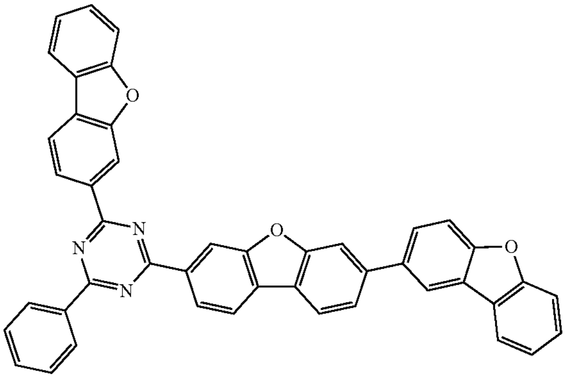
-continued
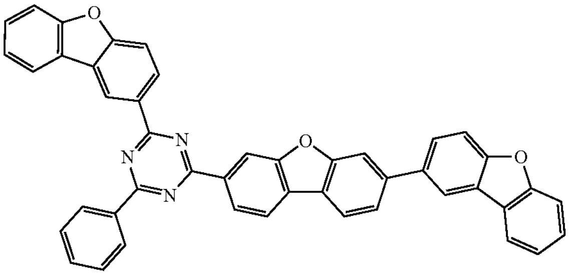
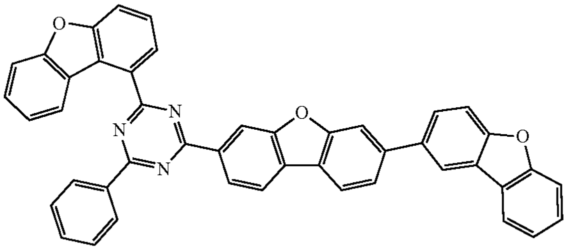
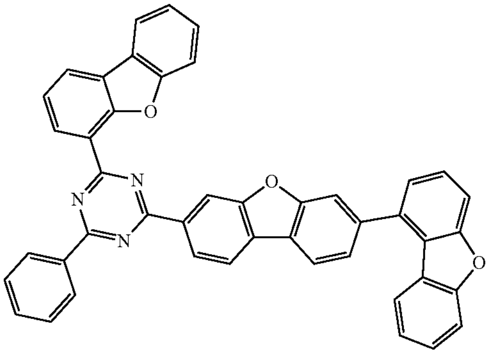
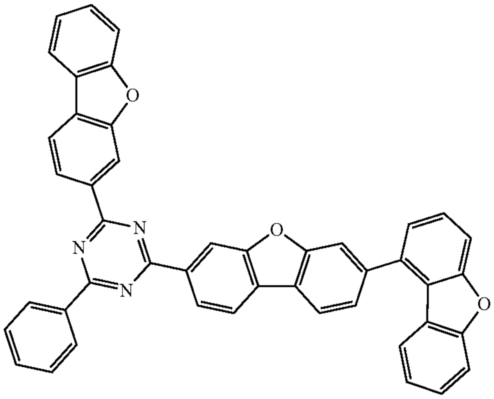
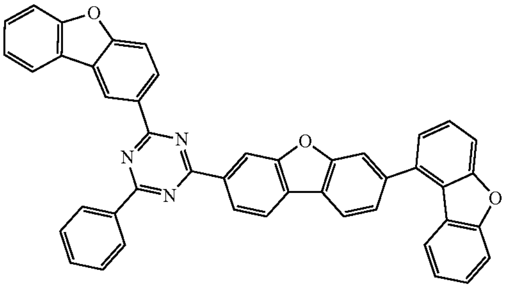

-continued

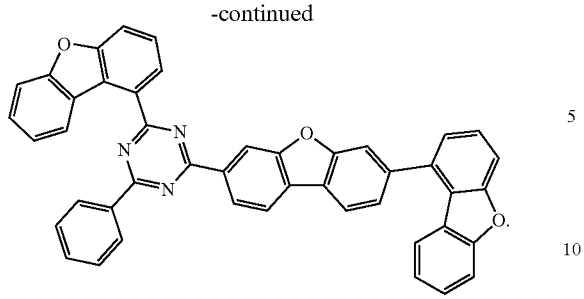

8. An organic light emitting device comprising: a first electrode; a second electrode provided to face the first electrode; and one or more organic material layers provided between the first electrode and the second electrode, wherein one or more layers of the organic material layers comprise the compound according to claim 1.

9. The organic light emitting device according to claim 8, wherein the organic material layer includes a light emitting layer, the light emitting layer includes two or more kinds of hosts, and one of the hosts is the compound.

* * * * *